US009867899B2

(12) United States Patent
Stewart

(10) Patent No.: US 9,867,899 B2
(45) Date of Patent: Jan. 16, 2018

(54) REINFORCED ADHESIVE COMPLEX COACERVATES AND METHODS OF MAKING AND USING THEREOF

(71) Applicant: UNIVERSITY OF UTAH RESEARCH FOUNDATION, Salt Lake City, UT (US)

(72) Inventor: Russell J. Stewart, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 15/131,583

(22) Filed: Apr. 18, 2016

(65) Prior Publication Data
US 2016/0250375 A1 Sep. 1, 2016

Related U.S. Application Data

(63) Continuation of application No. 13/114,397, filed on May 24, 2011, now abandoned.

(60) Provisional application No. 61/347,611, filed on May 24, 2010.

(51) Int. Cl.
A61L 24/02 (2006.01)
A61L 24/04 (2006.01)
A61L 24/06 (2006.01)
A61L 24/10 (2006.01)
D07B 3/00 (2006.01)
A61L 24/00 (2006.01)
A61L 27/26 (2006.01)
A61L 27/54 (2006.01)
C08F 8/00 (2006.01)
C08F 8/06 (2006.01)

(52) U.S. Cl.
CPC ......... A61L 24/046 (2013.01); A61L 24/0015 (2013.01); A61L 24/02 (2013.01); A61L 24/043 (2013.01); A61L 24/06 (2013.01); A61L 24/10 (2013.01); A61L 27/26 (2013.01); A61L 27/54 (2013.01); C08F 8/00 (2013.01); C08F 8/06 (2013.01); A61L 2300/62 (2013.01); A61L 2430/16 (2013.01)

(58) Field of Classification Search
CPC ...... A61B 5/0555; G03B 15/14; G03B 21/53; G03B 21/28; G03B 21/142
See application file for complete search history.

(56) References Cited

U.S. PATENT DOCUMENTS 3,458,460 A 7/1969 Shepard et al.
3,947,396 A 3/1976 Kangas et al.
3,950,296 A 4/1976 Kangas et al.
4,767,463 A 8/1988 Brode et al.
4,913,743 A 4/1990 Brode et al.
5,529,914 A 6/1996 Hubbell et al.
6,312,725 B1 11/2001 Wallace et al.
6,355,275 B1* 3/2002 Klein ...................... A61L 24/02
424/423
6,428,978 B1 8/2002 Olsen et al.
6,497,729 B1 12/2002 Moussey et al.
6,568,398 B2 5/2003 Cohen
6,916,488 B1 7/2005 Meier et al.
7,622,533 B2 11/2009 Lee
8,283,384 B2 10/2012 Stewart et al.
2001/0056301 A1 12/2001 Goupil et al.
2002/0006886 A1 1/2002 Beerse et al.
2002/0164364 A1 11/2002 Quong (Continued)

FOREIGN PATENT DOCUMENTS

| CN | 1341032 | 3/2002 |
| CN | 1446590 | 10/2003 |
| CN | 101405037 | 4/2009 |
| DE | 19810965 | 9/1999 |
| EP | 0632329 | 12/1997 |
| JP | 2003280056 | 12/1991 |
| JP | 2002166158 | 6/2002 |
| JP | 2009084224 | 4/2009 |
| JP | 2009084292 | 4/2009 |
| WO | 1995006056 | 3/1995 |
| WO | 2002092217 | 11/2002 |

(Continued)

OTHER PUBLICATIONS

Berg et al., "The Thermal Transition of a Non-Hydroxylated Form of Collagen. Evedence for a Role for Hydroxyproline in Stabilizing the Triple-Helix of Collagen", Biochem Biophys Res Commun, 1973, vol. 52, pp. 115-12.

(Continued)

Primary Examiner — Alma Pipic
(74) Attorney, Agent, or Firm — Gardner Groff Greenwald & Villanueva, PC

(57) ABSTRACT

Described herein is the synthesis of reinforced adhesive complex coacervates and their use thereof. The reinforced adhesive complex coacervates are composed of (a) at least one polycation, (b) at least one polyanion, and (c) a reinforcing component. The adhesive complex coacervates described herein can be subsequently cured to produce strong, cohesive adhesives. The reinforced adhesive complex coacervates have several desirable features when compared to conventional adhesives. The reinforced adhesive complex coacervates are effective in wet or underwater applications. The reinforced adhesive complex coacervates described herein, being phase separated from water, can be applied underwater without dissolving or dispersing into the water. The reinforced adhesive complex coacervates have numerous biological applications as bioadhesives and bioactive delivery devices. In particular, the reinforced adhesive complex coacervates described herein are particularly useful in underwater applications and situations where water is present such as, for example, wet tissues in physiological conditions.

23 Claims, 8 Drawing Sheets

(56) References Cited

U.S. PATENT DOCUMENTS

| | | |
|---|---|---|
| 2002/0169476 A1 | 11/2002 | Cohen |
| 2003/0023000 A1 | 1/2003 | Bavouzet et al. |
| 2004/0013738 A1 | 1/2004 | Voigt et al. |
| 2004/0086479 A1 | 5/2004 | Grinstaff et al. |
| 2005/0020734 A1 | 1/2005 | Asgarzadeh et al. |
| 2005/0147580 A1 | 7/2005 | Connor et al. |
| 2005/0220751 A1 | 10/2005 | Charmot et al. |
| 2005/0281883 A1 | 12/2005 | Daniloff et al. |
| 2006/0007528 A1 | 1/2006 | Cao et al. |
| 2006/0015083 A1 | 1/2006 | Munro |
| 2006/0039950 A1 | 2/2006 | Zhou et al. |
| 2006/0241242 A1 | 3/2006 | Devlin |
| 2006/0116682 A1 | 6/2006 | Longo |
| 2006/0122290 A1 | 6/2006 | Hubbell et al. |
| 2006/0156954 A1 | 7/2006 | Li et al. |
| 2006/0165804 A1* | 7/2006 | Lewis .................. A61K 9/1641 424/489 |
| 2006/0183848 A1 | 8/2006 | Maier et al. |
| 2006/0240064 A9 | 10/2006 | Hunter et al. |
| 2006/0275337 A1 | 12/2006 | Cohen Stuart et al. |
| 2006/0276371 A1 | 12/2006 | Schreiner et al. |
| 2007/0020469 A1 | 1/2007 | Wood et al. |
| 2007/0077276 A1 | 4/2007 | Haynie |
| 2007/0085059 A1 | 4/2007 | Mora-Guiterrez et al. |
| 2007/0191273 A1 | 8/2007 | Ambati et al. |
| 2007/0196454 A1 | 8/2007 | Stockman et al. |
| 2008/0003288 A1 | 1/2008 | Bromberg et al. |
| 2008/0075778 A1 | 3/2008 | Heller |
| 2008/0084000 A1 | 4/2008 | Forster |
| 2009/0162407 A1 | 6/2009 | Biggs et al. |
| 2010/0056474 A1 | 3/2010 | Baker et al. |
| 2010/0120923 A1 | 7/2010 | Stewart et al. |
| 2010/0291169 A1 | 11/2010 | Toreki et al. |
| 2010/0305626 A1 | 12/2010 | Stewart et al. |
| 2011/0054392 A1 | 3/2011 | Nies |
| 2011/0287067 A1 | 11/2011 | Stewart |
| 2011/0288274 A1 | 11/2011 | Russell et al. |
| 2012/0177918 A1 | 7/2012 | Stewart |
| 2013/0129787 A1 | 5/2013 | Stewart |
| 2013/0189313 A1 | 7/2013 | Stewart |
| 2014/0287061 A1 | 9/2014 | Landolina |

FOREIGN PATENT DOCUMENTS

| | | |
|---|---|---|
| WO | 2002100453 | 12/2002 |
| WO | 2005019421 | 3/2005 |
| WO | 2007024972 | 3/2007 |
| WO | 2007030811 | 3/2007 |
| WO | 2009094060 | 7/2009 |
| WO | 2011011658 | 1/2011 |
| WO | 2011028967 | 3/2011 |
| WO | 2011106595 | 9/2011 |
| WO | 2011149907 | 12/2011 |
| WO | 2012065148 | 5/2012 |

OTHER PUBLICATIONS

Hwang et al., "Expression of Functional Recombinant Mussel Adhesive Protein Mgfp-5 in *Escherichia coli*", Applied and Environmental Microbiology, 2004, vol. 70, No. 6, pp. 3352-3359.
Kamachi et al. "Synthesis of Block Polmers for Desalination Membranes. Preparation of Block Coplymers of 2-Vinylpyridine and Methacrylic Acid or Acrylic Acid", Macromolecules, 1972, vol. 5, No. 2, pp. 161-168.
Kayitmazer et al., "Mesophase Separation and Probe Dynamics in Protein-Polyelectrolyte Coacervates", Chemical Engineering Faculty Publications, 2007, vol. 3, pp. 1064-1076.
Lee et al. "Rapid Gel Formation and Adhesion in Photocurable and Biodegradable Block Copolymers with High DOPA Content", Macromolecules, 2006, vol. 39, pp. 1740-1748.
Lee et al., "Single-Molecule Mechanics of Mussel Adhesion", PNAS, 2006, vol. 103, No. 35, pp. 12999-13003.
Lee et al., "Synthesis of 3,4-dihydropxyphenylalanine (DOPA) Containing Monomers and their Co-Polymerization with PEG-Diacrylate to form Hydrogels", J. Biomater. Sci. Polymer Edn., 2004, vol. 15, No. 4, pp. 449-464.
Lim et al., "The Adhesive Properties of Coacervated Recombinant Hybrid mussel adhesive proteins", Biomaterials, 2010, vol. 31, No. 13, pp. 3715-3722.
Liu et al., "Chemistry of Periodate Mediated Cross-Linking of 3,4-Dihydroxlphenylalanine-Containing Molecules to Proteins", J. Am. Chem. Soc., 2006, vol. 128, pp. 15228-15235.
Mo et al., "Soft tissue adhesive composed of modified gelatin and polysaccharides." J. Biomater. Sci. Polymer Edn., 2000, vol. 11, No. 4, pp. 341-351.
Polyethyleneimine:EPOMIN, website, Nippon Shokubai, 2014.
Shao et al., "A Water-Borne Adhesive Modeled after the Sandcastle Glue of P. californica," Macromolecules Bioscience, vol. 9, Issue 5, Published Online Nov. 28, 2008, pp. 464-471.
Stevens et al., "Multiscale Structure of the Underwater Adhesive of Phragmatopoma Californica: A Nanostructured Latex with a Steep Microporosity Gradient", Langmuir, 2007, vol. 23, pp. 5045-5049.
Stewart et al., "The Tube Cement of Phragmatopoma Californica: A Solid Foam", The Journal of Experimental Biology, 2004, vol. 207, No. 26, pp. 4727-4734.
Wang et al., "A novel bioadhesive protein of silk filaments spun underwater by caddisfly larvae", Adv. Mater. Res., 2009, vol. 79-82, pp. 1631-1634.
Yu et al., "Synthetic Polypeptide Mimics of Marine Adhesives", Macromolecules, 1998, vol. 31, pp. 4739-4745.
Zhao et al., "Cement Proteins of the Tube-Building Polychaete Phragmatopoma Californica", J. Biol. Chem., 2005, vol. 280, No. 52, pp. 42938-42944.
Canadian Office Action for Application 2,712,843 dated Jul. 9, 2014.
Chinese First Office Action in CN Patent Application No. 200880128307.2 dated Oct. 27, 2011, pp. 13.
Chinese First Office Action in CN Patent Application No. 201180010546 dated Aug. 13, 2013 (English translation).
Chinese Office Action for Application 201080038397.3 dated Sep. 11, 2014.
Chinese Second Office Action in CN Patent Application 201080038397 dated Dec. 16, 2013; 4 pp.
First Examination Report for Indian Application 1584/MUMNP/2010 dated May 15, 2015.
International Search Report dated Aug. 26, 2013 for International Application No. PCT/US2013/029131.
International Search Report dated May 7, 2012 for International Application No. PCT/US/2011/060500.
International Search Report dated Nov. 22, 2010, for Application No. PCT/US10/43009.
ISR and WO dated Nov. 22, 2010 for PCT/US2010/043009.
Japanese First Office Action in JP Application No. 2012-521803 dated Aug. 6, 2014; 4 pp.
Japanese First Office Action in JP Application No. 2012-555168 dated Aug. 12, 2014; 2 pp.
Japanese Office Action for JP2012-555168 dated Jul. 21, 2015 with English Translation.
Notice of Preliminary Rejection from Korean Intellectual Property Office for Application 10-2010-7018637 dated Jan. 6, 2015.
Official Action for European Application 13 156 643.2-1302 dated Dec. 22, 2014.
PCT International Preliminary Report on Patentability for International Application No. PCT/US2008/083311, dated Jul. 27, 2010, pp. 10.
PCT International Search Report for International Search Report and the Written Opinion of the International Searching Authority, or the Declaration for International Application No. PCT/US2011/0376797, dated Sep. 13, 2011, pp. 9.
Supplementary European Search Report for EP Application No. 12804996 dated Feb. 19, 2015.
Supplementary European Search Report for European Application No. 10802933.1 dated Jun. 24, 2014, pp. 11.
Supplementary Extended European Search Report for European Application No. 08871349.0 dated Nov. 14, 2011, pp. 4.

(56) References Cited

OTHER PUBLICATIONS

Written Opinion of the International Searching Authority issued in PCT/US2011/26169 dated May 17, 2011.
Written Opinion of the International Searching Authority issued in PCT/US2012/044299 dated Nov. 16, 2012.
U.S. Advisory Action for U.S. Appl. No. 12/864,045 dated Sep. 23, 2014.
U.S. Advisory Action for U.S. Appl. No. 13/114,397 dated Mar. 23, 2015.
U.S. Advisory Action for U.S. Appl. No. 13/580,794 dated Nov. 13, 2014.
U.S. Advisory Action for U.S. Appl. No. 13/617,882 dated Oct. 16, 2015.
U.S. Advisory Action for U.S. Appl. No. 13/617,882 dated Sep. 18, 2014.
U.S. Office Action for U.S. Appl. No. 12/508,280 dated Sep. 20, 2011.
U.S. Office Action for U.S. Appl. No. 12/864,045 dated Jan. 5, 2015.
U.S. Office Action for U.S. Appl. No. 12/864,045 dated Jun. 18, 2014.
U.S. Office Action for U.S. Appl. No. 12/864,045 dated Oct. 7, 2013.
U.S. Office Action for U.S. Appl. No. 13/114,397 dated Dec. 17, 2015.
U.S. Office Action for U.S. Appl. No. 13/114,397 dated Feb. 27, 2014.
U.S. Office Action for U.S. Appl. No. 13/114,397 dated May 22, 2015.
U.S. Office Action for U.S. Appl. No. 13/114,397 dated Oct. 23, 2014.
U.S. Office Action for U.S. Appl. No. 13/295,061 dated Jan. 12, 2015.
U.S. Office Action for U.S. Appl. No. 13/295,061 dated Mar. 4, 2014.
U.S. Office Action for U.S. Appl. No. 13/580,794 dated Aug. 1, 2014.
U.S. Office Action for U.S. Appl. No. 13/580,794 dated Feb. 1, 2016.
U.S. Office Action for U.S. Appl. No. 13/580,794 dated Jan. 10, 2014.
U.S. Office Action for U.S. Appl. No. 13/580,794 dated May 12, 2015.
U.S. Office Action for U.S. Appl. No. 13/617,882 dated Apr. 4, 2016.
U.S. Office Action for U.S. Appl. No. 13/617,882 dated Aug. 27, 2013.
U.S. Office Action for U.S. Appl. No. 13/617,882 dated Jun. 15, 2015.
U.S. Office Action for U.S. Appl. No. 13/617,882 dated Jun. 5, 2014.
U.S. Office Action for U.S. Appl. No. 13/617,882 dated Nov. 19, 2014.
U.S. Office Action for U.S. Appl. No. 14/874,854 dated Feb. 24, 2016.
Chinese First Office Action for 201080038397 dated Apr. 3, 2013 (English summary).
Chinese First Office Action for 201180024981.8 dated Mar. 27, 2014 (English summary).
Chinese First Office Action for 201180050846.0 dated Apr. 3, 2014 (English summary).
Chinese Office Action for 2012800362923 dated Jan. 7, 2015 (English summary).
Chinese Second Office Action for 200880128307.2 dated Apr. 1, 2012 (translation).
Chinese Second Office Action for 201180010546 dated Jul. 2, 2014 (English summary).
Chinese Third Office Action for 201080038397 dated Aug. 21, 2014 (English summary).
International Search Report and Written Opinion for PCT/US08/083311 dated Jan. 6, 2009.

* cited by examiner

SEQUENCE LISTING

```
<160> NUMBER OF SEQ ID NOS: 17

<210> SEQ ID NO 1
<211> LENGTH: 191
<212> TYPE: PRT
<213> ORGANISM: Phragmatopoma californica

<400> SEQUENCE: 1

Met Lys Val Phe Ile Val Leu Ala Leu Val Ser Ala Ala Tyr Gly Cys
1               5                   10                  15

Gly Val Gly Ile Gly Cys Ala Gly Gly Arg Cys Gly Gly Ala Cys Gly
            20                  25                  30

Gly Lys Gly Tyr Gly Tyr Gly Gly Lys Leu Gly Tyr Gly Ala Tyr Gly
        35                  40                  45

Lys Gly Gly Ile Gly Gly Tyr Gly Tyr Gly Lys Gly Cys Val Gly Gly
    50                  55                  60

Tyr Gly Tyr Gly Gly Leu Gly Ala Gly Lys Leu Gly Gly Tyr Gly Tyr
65                  70                  75                  80

Gly Gly Ser Lys Cys Gly Gly Tyr Gly Tyr Gly Gly Gln Lys Leu Gly
                85                  90                  95

Gly Tyr Gly Tyr Gly Gly Lys Lys Leu Gly Gly Tyr Gly Tyr Ala Ala
            100                 105                 110

Lys Lys Val Gly Gly Tyr Gly Tyr Gly Ala Lys Lys Val Gly Gly Tyr
        115                 120                 125

Gly Tyr Gly Ala Lys Lys Val Gly Gly Tyr Gly Tyr Gly Ala Lys Lys
    130                 135                 140

Val Gly Gly Tyr Gly Tyr Gly Ala Lys Lys Val Gly Gly Tyr Gly Tyr
145                 150                 155                 160

Gly Ala Lys Lys Val Gly Gly Tyr Gly Tyr Gly Ala Lys Lys Val Gly
                165                 170                 175

Gly Tyr Gly Tyr Gly Val Lys Lys Val Gly Gly Tyr Gly Tyr Gly
            180                 185                 190

<210> SEQ ID NO 2
<211> LENGTH: 210
```

```
<212> TYPE: PRT
<213> ORGANISM: Phragmatopoma californica

<400> SEQUENCE: 2

Met Lys Val Leu Ile Phe Leu Ala Thr Val Ala Ala Val Tyr Gly Cys
1               5                   10                  15

Gly Gly Ala Gly Gly Trp Arg Ser Ser Cys Gly Gly Arg Trp Gly
            20                  25                  30

His Pro Ala Val His Lys Ala Leu Gly Gly Tyr Gly Tyr Gly Ala
        35                  40                  45

His Pro Ala Val His Ala Ala Val His Lys Ala Leu Gly Gly Tyr Gly
        50                  55                  60

Ala Gly Ala Tyr Gly Ala Gly Ala Trp Gly His Pro Ala Val His Lys
65                  70                  75                  80

Ala Leu Gly Gly Tyr Gly Ala Gly Ala Trp Gly His Pro Ala Val His
                85                  90                  95

Lys Ala Leu Gly Gly Tyr Gly Gly Tyr Gly Ala His Pro Ala Val His
                100                 105                 110

Val Ala Val His Lys Ala Leu Gly Gly Tyr Gly Ala Gly Ala Cys Gly
            115                 120                 125

His Lys Thr Gly Gly Tyr Gly Gly Tyr Gly Ala His Pro Val Ala Val
        130                 135                 140

Lys Ala Ala Tyr Asn His Gly Phe Asn Tyr Gly Ala Asn Asn Ala Ile
145                 150                 155                 160

Lys Ser Thr Lys Arg Phe Gly Gly Tyr Gly Ala His Pro Val Val Lys
                165                 170                 175

Lys Ala Phe Ser Arg Gly Leu Ser His Gly Ala Tyr Ala Gly Ser Lys
                180                 185                 190

Ala Ala Thr Gly Tyr Gly Tyr Gly Ser Gly Lys Ala Ala Gly Gly Tyr
            195                 200                 205

Gly Tyr
    210

<210> SEQ ID NO 3
<211> LENGTH: 272
<212> TYPE: PRT
<213> ORGANISM: Phragmatopoma californica

<400> SEQUENCE: 3

Met Pro Thr Leu Tyr Lys Lys Val Gly Lys Leu Val Ile Leu Ala Ile
1               5                   10                  15

Ile Val Thr Val Ala Ser Val Ala Ser Ala Gly Tyr Pro Thr Tyr Ser
            20                  25                  30

Pro Ser Gly Gly Thr His Ser Gly Tyr Asn Gly Pro His Gly Asn Val
        35                  40                  45

Val Lys Lys Thr Tyr Arg Gly Pro Tyr Gly Ala Gly Ala Ala Lys Ala
    50                  55                  60

Trp Asn Gly Tyr His Gly Ala Gly Tyr Thr Ser Val His His Gly Pro
65                  70                  75                  80

Ala Ser Thr Ser Trp His Thr Ser Trp Ser Asn Lys Lys Gly Gly Tyr
                85                  90                  95

Gly Tyr Gly Leu Lys Asn Lys Gly Tyr Gly Tyr Gly Leu Lys Lys Val
            100                 105                 110

Gly Tyr Gly Val Gly Leu His Ala Ala Gly Trp His Gly Val Gly Pro
        115                 120                 125
```

```
Tyr Gly Ala Gly Tyr His Gly Ala Gly Trp Asn Gly Leu Gly Tyr His
    130                 135                 140

Gly Ala Gly Tyr Gly Val His Gly Val Gly Leu His Gly Ala Gly Tyr
145                 150                 155                 160

Gly Leu His Gly Val Gly Leu His Gly Val Gly Tyr Gly Leu His Gly
            165                 170                 175

Val Gly Leu His Gly Ala Gly Tyr Gly Leu His Gly Val Gly Leu His
        180                 185                 190

Gly Ala Gly Tyr Gly Ile His Gly Val Gly Leu His Gly Ala Gly Tyr
            195                 200                 205

Gly Ile His Gly Val Gly Leu His Gly Val Gly Tyr Gly Leu His Gly
    210                 215                 220

Val Gly Leu His Gly Ala Gly Tyr Gly Leu His Gly Val Gly Leu His
225                 230                 235                 240

Gly Ala Gly Tyr Gly Ile His Gly Val Gly Leu His Gly Ala Gly Cys
            245                 250                 255

Gly Ile His Lys Thr Ala Cys Tyr Gly Val Gly Leu His Gly His Tyr
    260                 265                 270
```

<210> SEQ ID NO 4
<211> LENGTH: 144
<212> TYPE: PRT
<213> ORGANISM: Phragmatopoma californica

<400> SEQUENCE: 4

```
Met Lys Phe Leu Val Leu Leu Ala Leu Val Ala Ser Ala Ser Ala Tyr
1               5                   10                  15

Tyr Pro Leu Met Gly Gly Phe His Gly Gly Trp His Ala Pro Met Val
            20                  25                  30

His Gly Gly Leu Tyr His Gly Gly Trp His Ala Pro Met Val His Gly
        35                  40                  45

Gly Leu Tyr His Gly Gly Trp His Ala Pro Ile Val His Gly Gly Trp
    50                  55                  60

His Ala Pro Val Phe His Ala Pro Ala Pro Ile His Thr Val Ser His
65                  70                  75                  80

Ser Val Val Asn His Val Pro Met Met Pro Met Trp His His Pro Ala
            85                  90                  95

Pro Ala Pro Ala Pro Arg Pro Gly Arg Thr Ile Ile Leu Gly
        100                 105                 110

Gly Gly Lys Tyr Gly Pro Phe Gly Lys Tyr Gly Gly Ala Gly Leu
    115                 120                 125

Leu Ala Leu Gly Ala Leu Gly Gly Asn Gly Gly Phe Trp Lys Arg Arg
    130                 135                 140
```

<210> SEQ ID NO 5
<211> LENGTH: 328
<212> TYPE: PRT
<213> ORGANISM: Phragmatopoma californica

<400> SEQUENCE: 5

```
Met Leu Phe Tyr Asn Ala Asn Phe Val Gln Lys Ser Trp Val Leu Ile
1               5                   10                  15

Leu Leu Gly Leu Ala Ala Val Val Ala Cys Ser Glu Tyr Asp Lys Gly
            20                  25                  30

Leu Gly Gly Tyr Gly Arg Pro Ser Tyr Gly Gly Arg Arg Gly Tyr Gly
        35                  40                  45
```

```
Gly Arg Arg Gly Leu Gln Tyr His Gly Lys Tyr Gln Gly Arg Cys Glu
 50                  55                  60

Tyr Asp Gly Leu Tyr Phe Arg Asp Glu Lys Ser Phe Val Tyr Cys Ser
 65                  70                  75                  80

Asn Arg Asn Ser Tyr Ile Gln Pro Cys Ala Pro Gly Thr Arg Asn Ser
                 85                  90                  95

Pro Tyr Thr Lys Tyr Asn Arg Gly Ser Lys Tyr Asn Tyr Arg Asp Phe
             100                 105                 110

Cys Glu Val Asn Leu Val Asp Ser Gly Tyr Val Pro Lys Pro Gly Tyr
             115                 120                 125

Leu Pro Ala Pro Lys Lys Ala Tyr Pro Thr Lys Val Tyr Asp Leu Lys
130                 135                 140

Val Asp Tyr Ala Pro Lys Val Asp Tyr Ala Pro Lys Val Asp Tyr Ala
145                 150                 155                 160

Pro Lys Val Asp Tyr Ala Pro Lys Val Asp Tyr Val Ala Pro Lys Ala
                 165                 170                 175

Ser Tyr Val Pro Pro Lys Ala Ser Tyr Val Asp Pro Thr Pro Thr Tyr
             180                 185                 190

Gly Tyr Glu Ala Pro Phe Lys Gly Gly Tyr Asp Lys Pro Ser Tyr Gly
             195                 200                 205

Lys Asp Val Asp Thr Ser Tyr Glu Ser Lys Thr Thr Tyr Thr Val Glu
210                 215                 220

Lys Thr Ala Asp Lys Gly Tyr Gly Lys Gly Tyr Gly Asp Lys Glu Ile
225                 230                 235                 240

Ser Ala Lys Lys Ser Tyr Thr Leu Thr Glu Lys Arg Asp Tyr Asp Thr
                 245                 250                 255

Gly Tyr Asp Asn Ser Arg Ser Asp Glu Asp Ser Lys Glu Tyr Gly Tyr
             260                 265                 270

Asp Asn Asp Arg Ser Glu Ser Tyr Glu Arg Thr Glu Ser Tyr Thr Asp
             275                 280                 285

Glu Arg Thr Asp Gly Tyr Gly Gln Lys Val Glu Tyr Thr Gln Gln
290                 295                 300

Ser Glu Tyr Asp Arg Val Thr Arg Arg Gly Ile Trp Leu His Lys Gly
305                 310                 315                 320

Thr Glu Val Glu His Val Leu Tyr
                 325

<210> SEQ ID NO 6
<211> LENGTH: 136
<212> TYPE: PRT
<213> ORGANISM: Phragmatopoma californica
<220> FEATURE:
<221> NAME/KEY: misc_feature
<222> LOCATION: (49)..(49)
<223> OTHER INFORMATION: Xaa can be any naturally occurring amino acid

<400> SEQUENCE: 6

Met Asn Thr Phe Val Val Leu Ala Ala Ile Val Ala Val Ala Ala Cys
  1               5                  10                  15

Ser Gly Gly Tyr Asp Gly Arg Gln Tyr Thr Tyr Arg Gly Arg Tyr Asn
                 20                  25                  30

Asn Lys Cys Gly Asn Asp Gly Leu Tyr Phe Lys Asp Asp Lys Asn Phe
             35                  40                  45

Xaa Phe Cys Ser Asn Gly Asn Ser Tyr Val Gln Pro Cys Ala Pro Gly
 50                  55                  60

Thr Arg Asn Ser Gly Tyr Asn Asn Tyr Lys Gln Gly Ser Ile Tyr Asn
```

```
             65                  70                  75                  80
Tyr Arg Asp Phe Cys Asp Val Asn Leu Val Asp Glu Gly Tyr Gly Val
                    85                  90                  95

Gly Ala Lys Pro Gly Tyr Asn Lys Gly Tyr Asn Pro Gly Tyr Asn Pro
                100                 105                 110

Gly Tyr Gly Gly Tyr Asn Pro Gly Tyr Ser Thr Gly Tyr Gly Gly Tyr
            115                 120                 125

Lys Ala Gly Pro Gly Pro Tyr Trp
        130                 135

<210> SEQ ID NO 7
<211> LENGTH: 158
<212> TYPE: PRT
<213> ORGANISM: Phragmatopoma californica

<400> SEQUENCE: 7

Met Lys Leu Ala Leu Leu Leu Val Ala Val Cys Ala Ala Val Ala
1               5                   10                  15

Val Asn Ala Cys Gly Pro Leu Gly Cys Ser Gly Gly Tyr Gly Gly Val
                20                  25                  30

Leu Lys Cys Gly Val Gly Gly Cys Ala Leu Gly Gly Tyr Gly Gly Gly
            35                  40                  45

Tyr Ser Ala Gly Ile Gly Gly Tyr Gly Ile Lys Arg Leu Gly Cys Arg
        50                  55                  60

Gly Gly Arg Cys Gly Leu Arg Arg Val Gly Cys Arg Gly Gly Arg
65                  70                  75                  80

Cys Gly Leu Arg Gly Arg Leu Gly Cys Arg Gly Arg Cys Gly Leu
                85                  90                  95

Arg Lys Leu Gly Cys Arg Gly Gly Arg Cys Gly Leu Arg Gly Arg Leu
                100                 105                 110

Gly Cys Arg Gly Gly Arg Cys Gly Leu Arg Lys Arg Leu Gly Cys Arg
            115                 120                 125

Gly Gly Arg Cys Gly Arg Gly Gly Tyr Gly Gly Tyr Gly Gly Val
        130                 135                 140

Cys Ser Lys Gly Val Cys Gly Tyr Pro Ala Tyr Gly Lys
145                 150                 155

<210> SEQ ID NO 8
<211> LENGTH: 236
<212> TYPE: PRT
<213> ORGANISM: Phragmatopoma californica

<400> SEQUENCE: 8

Met Lys Val Ser Ile Ala Val Leu Ile Met Cys Cys Ile Ala Ala Val
1               5                   10                  15

Leu Ala Asp Gly Tyr Lys Ser Lys Asn Gly Gly Gln Ala Gly Gly Tyr
                20                  25                  30

Gly Gly Tyr Gly Ser Gly Tyr Gly Gly Tyr Gly Gly Gly Tyr Asp
            35                  40                  45

Gly Gly Tyr Gly Gly Glu Lys Gly Lys Ser Gly Lys Gly Tyr Gly Asp
        50                  55                  60

Arg Lys Gly Lys Ser Glu Lys Gly Tyr Gly Asn Gly Lys Gly Lys Gly
65                  70                  75                  80

Gly Ser Gly Tyr Gly Gly Tyr Asp Gly Tyr Gly Gly Lys
                85                  90                  95

Gly Lys Ser Gly Ser Gly Tyr Gly Gly Gly Tyr Asp Gly Gly Tyr Gly
```

```
                    100                 105                 110
Gly Gly Lys Gly Lys Ser Gly Ser Gly Tyr Gly Gly Tyr Asp Gly
                115                 120                 125
Gly Tyr Asp Gly Gly Tyr Gly Gly Lys Gly Lys Ser Gly Ser Gly
            130                 135                 140
Phe Gly Gly Tyr Asp Gly Gly Tyr Asp Gly Gly Tyr Gly Gly Gly
145                 150                 155                 160
Lys Gly Lys Ser Gly Ser Gly Tyr Gly Gly Tyr Asp Gly Gly Tyr
                165                 170                 175
Asp Gly Gly Tyr Gly Gly Lys Gly Lys Ser Gly Ser Gly Tyr Gly
            180                 185                 190
Gly Gly Tyr Asp Gly Gly Tyr Asp Gly Gly Tyr Gly Gly Lys Gly
        195                 200                 205
Lys Ser Gly Ser Gly Tyr Gly Gly Tyr Asp Gly Gly Tyr Asp Gly
        210                 215                 220
Arg Tyr Gly Gly Lys Gly Lys Ser Gly Ser Gly
225                 230                 235

<210> SEQ ID NO 9
<211> LENGTH: 191
<212> TYPE: PRT
<213> ORGANISM: Phragmatopoma californica

<400> SEQUENCE: 9

Met Lys Leu Ile Cys Leu Val Leu Leu Ala Val Cys Ile Val Ala Val
1               5                   10                  15
Ser Ala Ser Ser Ser Gly Gly Arg Arg Arg Val Ile Val Ile
            20                  25                  30
Gly Asn Arg Gly Arg Ala Pro Ala Arg Pro Arg Ser Asn Ile His Tyr
            35                  40                  45
His Met His Ala Pro Gln Pro Arg Met Met Met Ala Pro Arg Met Met
        50                  55                  60
Met Ala Pro Met Met Met Ala Pro Met Ala Met Pro Ala Thr Ser His
65                  70                  75                  80
Val Tyr Gln Ser Val Ser Tyr Pro Gly Ala Met Tyr Arg Tyr Gly Leu
                85                  90                  95
Gly Ser Leu Gly Gly Gly Phe Ile Ser Gly Gly Leu Gly Gly Ile Val
            100                 105                 110
Gly Gly Gly Leu His Gly Gly Val Thr Ser Gly Leu His Gly Gly
        115                 120                 125
Val Val Thr Ser Gly Leu His Gly Gly Val Val Thr Ser Gly Leu His
        130                 135                 140
Gly Gly Leu Val Ser Gly Gly Trp His Ser Gly Val Val Ser His Gly
145                 150                 155                 160
Gly Leu Ile Gly Gly Ile His Thr Thr Tyr Gly Gly Phe His Lys
                165                 170                 175
Gly Val Val His Gly Gly Tyr Thr Gly His Tyr Gly Lys Arg Arg
            180                 185                 190

<210> SEQ ID NO 10
<211> LENGTH: 102
<212> TYPE: PRT
<213> ORGANISM: Phragmatopoma californica

<400> SEQUENCE: 10

Met Lys Leu Ala Val Phe Ala Leu Leu Val Ala Phe Ala Ile Val Tyr
```

```
                1               5                  10                  15
             Thr Ala Glu Gly Leu Val Tyr Gly Gly Gln Lys Gly Tyr Gly Tyr Gly
                            20                  25                  30
             Gly Lys Gly Tyr Gly Tyr Gly Cys Thr Gly Gly Tyr Gly Leu Tyr Gly
                            35                  40                  45
             Gly Lys Gly Tyr Gly Tyr Gly Lys Gly Tyr Gly Tyr Gly Cys Arg Gly
                            50                  55                  60
             Gly Tyr Gly Tyr Gly Lys Gly Tyr Gly Tyr Gly Lys Tyr Arg Gly
             65                  70                  75                  80
             Tyr Gly Tyr Gly Asn Lys Val Gly Tyr Gly Tyr Gln Gln Leu Gly
                            85                  90                  95
             Tyr Lys Asn Gly Arg Lys
                            100

<210> SEQ ID NO 11
<211> LENGTH: 91
<212> TYPE: PRT
<213> ORGANISM: Phragmatopoma californica

<400> SEQUENCE: 11

Leu Asp Gly Gly Cys Lys Pro Thr Gly Gly Phe Ile Lys Gly Ser Val
             1               5                  10                  15
             Gly Pro Cys Gly Gly Tyr Asn His Gln His Val Val Gly Pro Asn Gly
                            20                  25                  30
             Ala His Gly Arg Arg Val Gly Tyr Gly Pro Asn Gly Lys Tyr Ser Gln
                            35                  40                  45
             Ile Tyr Gly Asn Gly Pro Gly Gly Arg Tyr Ser His Thr Val Val Tyr
                            50                  55                  60
             Pro Arg Val Arg Pro Tyr Gly Gly Tyr Gly Phe Lys Gly Gly Tyr Gly
             65                  70                  75                  80
             Gly Tyr His Gly Val Gly Tyr Lys Gly Gly Tyr
                            85                  90

<210> SEQ ID NO 12
<211> LENGTH: 145
<212> TYPE: PRT
<213> ORGANISM: Phragmatopoma californica

<400> SEQUENCE: 12

Met Lys Val Phe Val Ala Ala Leu Leu Leu Cys Cys Ile Ala Ala Ala
             1               5                  10                  15
             Ala Ala Glu Asp Gly Tyr Gly Phe Gly Tyr Asp Gly Tyr Gly Ser Gly
                            20                  25                  30
             Tyr Gly Tyr Asp Gly Tyr Ser Tyr Gly Gly Asp Lys Gly Tyr Gly Tyr
                            35                  40                  45
             Gly Lys Gly Lys Gly Tyr Gly Tyr Glu Gly Gly Lys Gly Tyr Gly Tyr
                            50                  55                  60
             Glu Gly Gly Lys Gly Tyr Gly His Glu Glu Gly Lys Gly Tyr Gly His
             65                  70                  75                  80
             Glu Gly Gly Lys Gly Tyr Gly Tyr Glu Gly Gly Lys Gly Tyr Gly Tyr
                            85                  90                  95
             Gly Gly Gly Lys Gly Tyr Gly His Asp Gly Gly Lys Gly Tyr Gly His
                            100                 105                 110
             Asp Gly Gly Lys Gly Tyr Gly Tyr Gly Gly Lys Gly Tyr Gly His
                            115                 120                 125
             Glu Gly Gly Lys Gly Tyr Gly Tyr Glu Gly Gly Lys Gly Tyr Gly Lys
```

-continued

```
              130                 135                 140
Tyr
145

<210> SEQ ID NO 13
<211> LENGTH: 134
<212> TYPE: PRT
<213> ORGANISM: Phragmatopoma californica

<400> SEQUENCE: 13

Met Arg Ile Val Ile Cys Leu Leu Val Leu Val Ala Gly Ala Tyr Gly
1               5                   10                  15

Ile Gly Cys Gly Tyr Gly Gly Tyr Gly Gly Tyr Gly Gly Phe His
            20                  25                  30

Gly Gly Tyr Ile Gly Tyr His Gly Gly Tyr Pro Gly Tyr Ser Gly Gly
        35                  40                  45

Phe Arg Gly Tyr Gly Tyr Pro Gly Arg Val His Thr Asn Val Val His
    50                  55                  60

His Asn Ile Pro Val Phe Met Pro Pro Met Pro Arg Arg Ala Pro
65                  70                  75                  80

Ala Pro Ala Pro Arg Gly Arg Thr Ile Ile Leu Gly Gly Gly Lys Tyr
                85                  90                  95

Gly Leu Phe Gly Lys Lys Ser Lys Asn Lys Gly Phe Gly Gly Leu Gly
            100                 105                 110

Val Leu Ser Leu Leu Gly Gly Leu Gly Gly Lys Gly Gly Gly Ile
        115                 120                 125

Arg Phe Leu Gly Arg Lys
    130

<210> SEQ ID NO 14
<211> LENGTH: 226
<212> TYPE: PRT
<213> ORGANISM: Phragmatopoma californica

<400> SEQUENCE: 14

Met Lys Val Ile Ile Leu Leu Ala Thr Val Ala Ala Val Tyr Gly Cys
1               5                   10                  15

Gly Gly Trp Asn Gly Gly Phe Gly Gly Gly Lys Ala Cys Gly Gly Gly
            20                  25                  30

Trp Gly Ala Lys Ala Leu Gly Gly Tyr Gly Ser Tyr Asn Gly Asn Gly
        35                  40                  45

Tyr Gly Ala His Pro Val Ala Val Lys Ser Ala Phe Asn Lys Gly Val
    50                  55                  60

Ser Tyr Gly Ala Arg Ser Ala Val Lys Ala Thr Arg Gly Phe Ala Tyr
65                  70                  75                  80

Gly Lys Gly Ser Ser Tyr Gly Tyr Gly Ala His Pro Ala Val Lys Ser
                85                  90                  95

Ala Phe Gly Asn Gly Phe Lys Thr Gly Ala His Ala Ala Val Asn Gly
            100                 105                 110

Tyr Gly Tyr Gly Ala Val Lys Ser Ala Leu Ser Gly Gly Tyr Gly Tyr
        115                 120                 125
```

```
Gly Ser Tyr Gly Ala His Pro Ala Val Lys Ser Ala Tyr Arg Lys Gly
        130                 135                 140

Leu Ser Tyr Gly Ala Lys Ser Ala Val Lys Ala Thr Arg Gly Phe Ala
145                 150                 155                 160

Tyr Gly Arg Ser Gly Tyr Gly Ala His Pro Val Val Lys Ser Ala Phe
                165                 170                 175

Ser Asn Gly Phe Lys Tyr Gly Ala His Ala Ala Val Lys Ala Thr Asn
            180                 185                 190

Gly Tyr Gly Tyr Gly Ala Val His Pro Ala Val Lys Ala Ala Val Lys
        195                 200                 205

Gly Gly Tyr Gly Tyr Gly Asn Lys Gly Gly Tyr Gly Ala Gly Tyr Ala
        210                 215                 220

Ala Tyr
225

<210> SEQ ID NO 15
<211> LENGTH: 89
<212> TYPE: PRT
<213> ORGANISM: Phragmatopoma californica

<400> SEQUENCE: 15

Met Lys Val Phe Val Ala Thr Leu Leu Leu Cys Cys Ile Ala Ala Ala
1               5                   10                  15

Ala Ala Ala Gly Tyr Gly Asn Gly Tyr Ala Tyr Gly Ser Gly Tyr
            20                  25                  30

Ala Gly Tyr Gly Thr Gly Tyr Ala Gly Tyr Gly Ser Gly Tyr Gly Tyr
        35                  40                  45

Asp Gly Tyr Gly Tyr Gly Gly Lys Gly Tyr Gly Tyr Gly Gly Asp
    50                  55                  60

Lys Gly Tyr Gly Tyr Gly Gly Lys Gly Tyr Gly Tyr Gly Gly Gln Lys
65                  70                  75                  80

Gly Tyr Gly Tyr Gly Tyr Gly Lys Tyr
                85

<210> SEQ ID NO 16
<211> LENGTH: 105
<212> TYPE: PRT
<213> ORGANISM: Phragmatopoma californica

<400> SEQUENCE: 16

Met Lys Leu Leu Leu Leu Phe Ala Leu Ala Ala Val Ala Val Ala Leu
1               5                   10                  15

Pro Tyr Gly Tyr Ser Gly Lys Pro Gly Tyr Gly Tyr Asp Ala Val Asp
                20                  25                  30

Ala Val Tyr Asn Arg Leu Ala Asp Lys Gln Gln Ala Val Asn Arg Lys
            35                  40                  45

Ala Glu Tyr Val Gly Ala Gly Thr Gly Thr Ala Lys Tyr Asn Gly Val
        50                  55                  60

Pro Gly Ala Asn Tyr Gly Tyr Glu Asn Asp Arg Lys Tyr Gly Tyr Asp
65                  70                  75                  80
```

Asn Lys Gly Tyr Gly Gly Tyr Gly Asp Lys Gly Tyr Gly Tyr Gly
                85                  90                  95

Asp Lys Gly Leu Tyr Asp Gly Tyr Tyr
            100                 105

<210> SEQ ID NO 17
<211> LENGTH: 275
<212> TYPE: PRT
<213> ORGANISM: Phragmatopoma californica

<400> SEQUENCE: 17

Lys Tyr Tyr Asp Asp Glu Lys Arg Asp Ala Lys Tyr Arg Lys Pro
1               5                   10                  15

Ser Tyr Asn Pro Tyr Asn Thr Tyr Lys Asp Tyr Pro Pro Lys Lys Ile
                20                  25                  30

Tyr Asn Asp Asp Glu Lys Arg Asp Ala Asp Gln Tyr Arg Ile Ser Tyr
                35                  40                  45

Asn Pro Tyr Asn Thr Tyr Lys Asp Tyr Pro Pro Lys Lys Lys Tyr Tyr
            50                  55                  60

Asp Asp Glu Lys Arg Asp Ala Tyr Lys Tyr Arg Asn Pro Ser Tyr Asn
65                  70                  75                  80

Pro Tyr Asn Thr Tyr Lys Asp Tyr Pro Pro Lys Lys Ile Tyr Tyr Asp
                85                  90                  95

Asp Glu Lys Arg Asp Ala Asp Gln Tyr Arg Asn Pro Ser Tyr Asn Pro
            100                 105                 110

Tyr Asn Thr Tyr Lys Asp Tyr Pro Pro Lys Lys Lys Tyr Tyr Asp Asp
            115                 120                 125

Glu Lys Arg Asp Ala Asp Gln Tyr Arg Asn Pro Ser Tyr Asn Pro Tyr
    130                 135                 140

Asn Thr Tyr Lys Asp Tyr Leu Pro Lys Lys Lys Tyr Tyr Asp Asp Glu
145                 150                 155                 160

Lys Arg Asp Ala Asp Gln Tyr Arg Lys Pro Ser Tyr Asn Pro Tyr Asn
                165                 170                 175

Ser Tyr Lys Asp Tyr Pro Pro Lys Lys Lys Tyr Tyr Asp Asp Glu Lys
            180                 185                 190

Arg Asp Ala Asp Gln Tyr Arg Asn Pro Ser Tyr Asn Pro Tyr Asn Thr
    195                 200                 205

Tyr Lys Asp Tyr Leu Pro Lys Lys Lys Tyr Tyr Asp Asp Glu Lys Arg
    210                 215                 220

Asp Ala Asp Gln Tyr Arg Asn Pro Ser Tyr Asn Pro Tyr Asn Thr Tyr
225                 230                 235                 240

Lys Asp Tyr Pro Pro Lys Lys Lys Tyr Tyr Asp Asp Glu Lys Arg Asp
            245                 250                 255

Ala Asp Gln Tyr Arg Asn Pro Ser Tyr Asn Pro Tyr Asn Thr Tyr Lys
            260                 265                 270

Asp Tyr Pro
        275

REINFORCED ADHESIVE COMPLEX COACERVATES AND METHODS OF MAKING AND USING THEREOF

CROSS REFERENCE TO RELATED APPLICATION

This application is a continuation application of U.S. application Ser. No. 13/114,397, filed May 24, 2011, which claims priority upon U.S. Provisional Application Ser. No. 61/347,611, filed May 24, 2010. These applications are hereby incorporated by reference in their entirety for all of their teachings.

ACKNOWLEDGEMENTS

This invention was made with government support under grant EB006463 awarded by the National Institutes of Health and N00014-10-1-0108 awarded by the Office of Naval Research. The government has certain rights in the invention.

CROSS REFERENCE TO SEQUENCE LISTING

Proteins described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Bone fractures are a serious health concern in society today. In addition to the fracture itself, a number of additional health risks are associated with the fracture. For example, intra-articular fractures are bony injuries that extend into a joint surface and fragment the cartilage surface. Fractures of the cartilage surface often lead to debilitating posttraumatic arthritis. The main determining factors in the development of posttraumatic arthritis are thought to be the amount of energy imparted at the time of injury, the patient's genetic predisposition (or lack thereof) to posttraumatic arthritis, and the accuracy and maintenance of reduction. Of the three prognostic factors, the only factor controllable by orthopedic caregivers is achievement and maintenance of reduction. Comminuted injuries of the articular surface (the cartilage) and the metaphysis (the portion of the bone immediately below the cartilage) are particularly challenging to maintain in reduced (aligned) position. This relates to the quality and type of bone in this area. It also relates to the limitations of fixation with titanium or stainless steel implants.

Currently, stainless steel and titanium implants are the primary methods of fixation, but their size and the drilling necessary to place them frequently interfere with the exact manipulation and reduction of smaller pieces of bone and cartilage. A variety of bone adhesives have been tested as alternatives to mechanical fixation. These fall into four categories: polymethylmethacrylates (PMMA), fibrin-based glues, calcium phosphate (CP) cements, and CP resin composites. PMMA cements, which are used in the fixation of protheses, have well-known drawbacks, one of the most serious being that the heat generated from the exothermic setting reaction can kill adjacent bone tissue. Also, the poor bonding to bone leads to aseptic loosening, the major cause of PMMA cemented prothesis failure.

Fibrin glues, based on the blood clotting protein fibrinogen, have been tested for fixing bone grafts and repairing cartilage since the 1970s and yet have not been widely deployed. One of the drawbacks of fibrin glues is that they are manufactured from pooled human donor blood. As such, they carry risk of transmitting infections and could potentially be of limited supply.

CP cements are powders of one or more forms of CP, e.g., tetracalcium phosphate, dicalcium phosphate anhydride, and β-tricalcium phosphate. When the powder is mixed with water it forms a paste that sets up and hardens through the entanglement of one or more forms of CP crystals, including hydroxyapatite. Advantages of CP cements include isothermal set, proven biocompatibility, osteoconductivity, and they serve as a reservoir for Ca and $PO_4$ for hydroxyapatite formation during healing. The primary disadvantages are that CP cements are brittle, have low mechanical strength and are therefore not ideal for stable reduction of small articular segments. CP cements are used mostly as bone void fillers. The poor mechanical properties of CP cements have led to composite cements of CP particles and polymers. By varying the volume fractions of the particulate phase and the polymer phase, the modulus and strength of the glue can be adjusted toward those of natural bone, an avenue that is also open to us.

Given the overall health impact associated with bone fractures and the imperfect state of current fixation methods, new fixation methods are needed. Thus, what is needed are bioadhesives with increased bond strengths. The bioadhesives should have good adherence to wet substrates such as bone, membranes, and tissues. Finally, the bioadhesives should be easy to produce, handle, and store.

SUMMARY

Described herein is the synthesis of reinforced adhesive complex coacervates and their use thereof. The reinforced adhesive complex coacervates are composed of (a) at least one polycation, (b) at least one polyanion, and (c) a reinforcing component. The adhesive complex coacervates described herein can be subsequently cured to produce strong, cohesive adhesives. The reinforced adhesive complex coacervates have several desirable features when compared to conventional adhesives. The reinforced adhesive complex coacervates are effective in water-based applications. The reinforced adhesive complex coacervates described herein have low interfacial tension with water and wettable substrates. When applied to a wet substrate they spread over the interface rather than beading up. The reinforced adhesive complex coacervates have numerous biological applications as bioadhesives and drug delivery devices. In particular, the reinforced adhesive complex coacervates described herein are particularly useful in underwater applications and situations where water is present such as, for example, physiological conditions.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
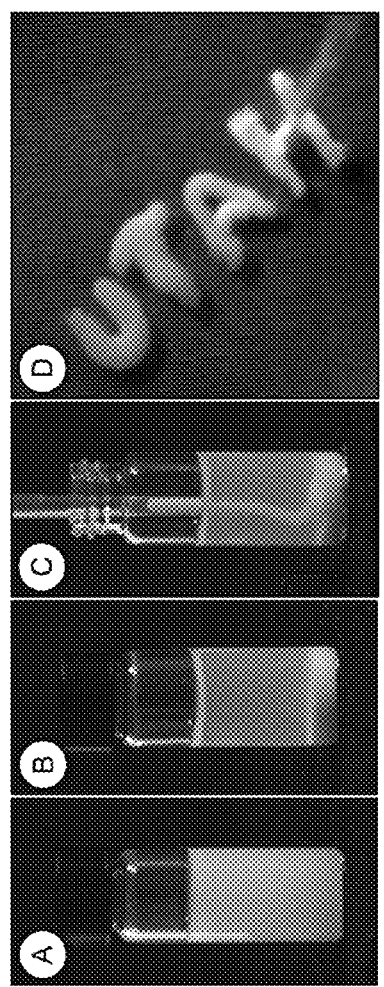
FIG. 1 shows the formation of complex coacervates by adjusting the pH of a solution of polycations and polyanions. (A) Oppositely charged polycations and polyanions associate into colloidal polyelectrolyte complexes (PECs) at a pH (~6 for the example shown) where the PECs have a net positive charge as represented in (E). (B) By raising the pH (to ~7 for the example shown), the net charge on the colloidal PECs approaches net charge neutrality where upon the complexes associate and separate as a dense fluid phase, i.e., a complex coacervate. (C) The complex coacervate has several ideal properties as the basis of underwater adhesives: density greater than water so they sink rather than float, water immiscibility that prevents mixing in a watery environment, and injectability allowing convenient application onto wet surfaces or underwater. (D) The complex coacervates can readily be spread on wet hydrophilic substrates because of the low interfacial tension with water and wettable surfaces.
Figure 1:
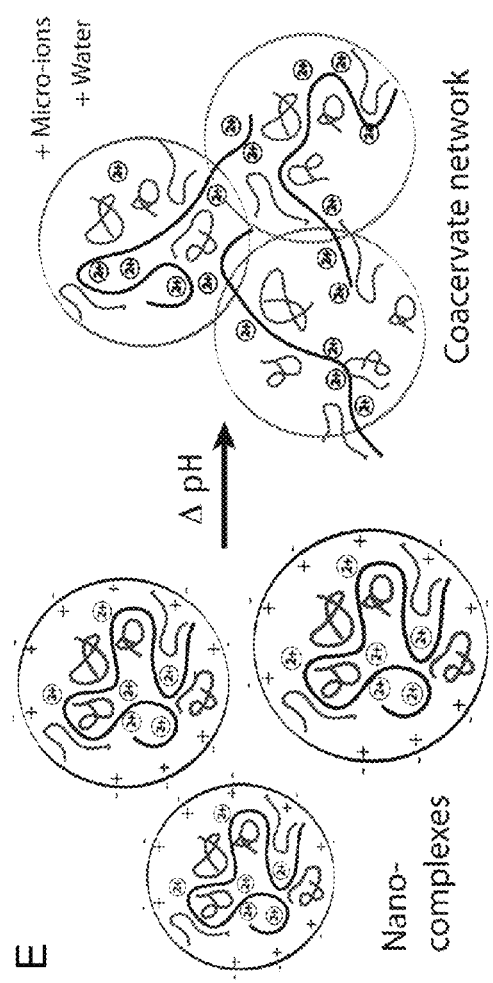

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, a palmitate group. A "lower alkyl" group is an alkyl group containing from one to six carbon atoms.

The term "aryl group" as used herein is any carbon-based aromatic group including, but not limited to, benzene, naphthalene, etc. The term "aryl group" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

Described herein are reinforced adhesive complex coacervates and their applications thereof. In general, the complex coacervates are a mixture of polycations and polyanions in balanced proportions to produce a phase separated fluid at a desired pH. The reinforced adhesive complex coacervate comprises at least one polycation, at least one polyanion, and a reinforcing component.

The adhesive complex coacervate is an associative liquid with a dynamic structure in which the individual polymer components can diffuse throughout the entire phase. As described above, the adhesive complex coacervates exhibit low interfacial tension with water and hydrophilic substrates. In other words, when applied to substrates either under water or that are wet the complex coacervate spreads evenly over the interface rather than beading up and penetrates cracks and defects. Additionally, upon intermolecular crosslinking (discussed in detail below), the adhesive complex coacervate forms a strong, insoluble, cohesive material. Conversely, polyelectrolyte complexes (PECs), which can be a precursor to the adhesive complex coacervates described herein, are small colloidal particles.

An exemplary model of the differences in phase behavior between the polyelectrolyte complexes (PEC) and the adhesive complex coacervate is presented in FIG. 1. At low pH the oppositely charged polyelectrolytes associate electrostatically into nano-complexes with a net positive surface charge that stabilizes the suspension (FIG. 1A). With increasing pH the net charge of the complexes approaches net neutrality (FIG. 1B). Thus, in certain aspects, the conversion of the PEC to complex coacervate can be "triggered" by adjusting the pH and/or the concentration of the multivalent cation. For example, the PECs can be produced at a pH of less than or equal to 4, and the pH of the PECs can be raised to greater than or equal to 7.0, from 7.0 to 9.0, or from 8.0 to 9.0 to convert the PECs to a complex coacervate. Alternatively, a solution of polycation can be mixed with a solution of polyanion such that when the two solutions are mixed the final pH of the mixture is conducive to the formation of the complex coacervate. In this embodiment, the concentration of the polycation and polyanion can be adjusted accordingly in order to produce a complex coacervate.

Each component used to prepare the reinforced adhesive complex coacervates and methods for making and using the same are described below.

I. Polycations

The polycation is generally composed of a polymer backbone with a plurality of cationic groups at a particular pH. The cationic groups can be pendant to the polymer backbone and/or incorporated within the polymer backbone. In certain aspects, (e.g., biomedical applications), the polycation is any biocompatible polymer possessing cationic groups or groups that can be readily converted to cationic groups by adjusting the pH. In one aspect, the polycation is a polyamine compound. The amino groups of the polyamine can be branched or part of the polymer backbone. The amino group can be a primary, secondary, or tertiary amino group that can be protonated to produce a cationic ammonium group at a selected pH. In general, the polyamine is a polymer with a large excess of positive charges relative to negative charges at the relevant pH, as reflected in its isoelectric point (pI), which is the pH at which the polymer has a net neutral charge. The number of amino groups present on the polycation ultimately determines the charge of the polycation at a particular pH. For example, the polycation can have from 10 to 90 mole %, 10 to 80 mole %, 10 to 70 mole %, 10 to 60 mole %, 10 to 50 mole %, 10 to 40 mole %, 10 to 30 mole %, or 10 to 20 mole % amino groups. In one aspect, the polyamine has an excess positive charge at a pH of about 7, with a pI significantly greater than 7. As will be discussed below, additional amino groups can be incorporated into the polymer in order to increase the pI value.

In one aspect, the amino group can be derived from a residue of lysine, histidine, or arginine attached to the polycation. Any anionic counterions can be used in association with the cationic polymers. The counterions should be physically and chemically compatible with the essential components of the composition and do not otherwise unduly impair product performance, stability or aesthetics. Non-limiting examples of such counterions include halides (e.g., chloride, fluoride, bromide, iodide), sulfate and methylsulfate.

In one aspect, the polycation can be a positively-charged protein produced from a natural organism. For example, a recombinant *P. californica* protein can be used as the polycation. In one aspect, Pc1, Pc2, Pc4-Pc18 (SEQ ID NOS 1-17) can be used as the polycation. The type and number of amino acids present in the protein can vary in order to achieve the desired solution properties. For example, Pc1 is enriched with lysine (13.5 mole %) while Pc4 and Pc5 are enriched with histidine (12.6 and 11.3 mole %, respectively).

In another aspect, the polycation is a recombinant protein produced by artificial expression of a gene or a modified gene or a composite gene containing parts from several genes in a heterologous host such as, for example, bacteria, yeast, cows, goats, tobacco, and the like.

In another aspect, the polycation can be a biodegradable polyamine. The biodegradable polyamine can be a synthetic polymer or naturally-occurring polymer. The mechanism by which the polyamine can degrade will vary depending upon the polyamine that is used. In the case of natural polymers, they are biodegradable because there are enzymes that can hydrolyze the polymers and break the polymer chain. For example, proteases can hydrolyze natural proteins like gelatin. In the case of synthetic biodegradable polyamines, they also possess chemically labile bonds. For example, β-aminoesters have hydrolyzable ester groups. In addition to the nature of the polyamine, other considerations such as the molecular weight of the polyamine and crosslink density of the adhesive can be varied in order to modify the degree of biodegradability.

In one aspect, the biodegradable polyamine includes a polysaccharide, a protein, or a synthetic polyamine. Polysaccharides bearing one or more amino groups can be used herein. In one aspect, the polysaccharide is a natural polysaccharide such as chitosan or chemically modified chitosan. Similarly, the protein can be a synthetic or naturally-occurring compound. In another aspect, the biodegradable polyamine is a synthetic polyamine such as poly(β-aminoesters), polyester amines, poly(disulfide amines), mixed poly(ester and amide amines), and peptide crosslinked polyamines.

In the case when the polycation is a synthetic polymer, a variety of different polymers can be used; however, in certain applications such as, for example, biomedical applications, it is desirable that the polymer be biocompatible and non-toxic to cells and tissue. In one aspect, the biodegradable polyamine can be an amine-modified natural polymer. For example, the amine-modified natural polymer can be gelatin modified with one or more alkylamino groups, heteroaryl groups, or an aromatic group substituted with one or more amino groups. Examples of alkylamino groups are depicted in Formulae IV-VI

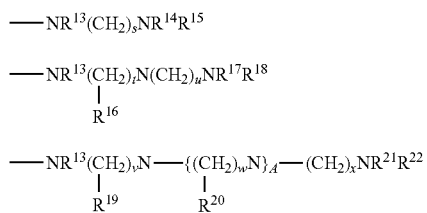

wherein $R^{13}$-$R^{22}$ are, independently, hydrogen, an alkyl group, or a nitrogen containing substituent;
s, t, u, v, w, and x are an integer from 1 to 10; and
A is an integer from 1 to 50,
where the alkylamino group is covalently attached to the natural polymer. In one aspect, if the natural polymer has a carboxyl group (e.g., acid or ester), the carboxyl group can be reacted with an alkylamino compound to produce an amide bond and incorporate the alkylamino group into the polymer. Thus, referring to formulae IV-VI, the amino group $NR^{13}$ is covalently attached to the carbonyl group of the natural polymer.

As shown in formula IV-VI, the number of amino groups can vary. In one aspect, the alkylamino group is —NHCH$_2$NH$_2$, —NHCH$_2$CH$_2$NH$_2$, —NHCH$_2$CH$_2$CH$_2$NH$_2$, —NHCH$_2$CH$_2$CH$_2$CH$_2$NH$_2$, —NHCH$_2$CH$_2$CH$_2$CH$_2$CH$_2$NH$_2$, —NHCH$_2$NHCH$_2$CH$_2$CH$_2$NH$_2$, —NHCH$_2$CH$_2$NHCH$_2$CH$_2$CH$_2$NH$_2$, —NHCH$_2$CH$_2$CH$_2$NHCH$_2$CH$_2$CH$_2$CH$_2$NHCH$_2$CH$_2$CH$_2$NH$_2$, —NHCH$_2$CH$_2$NHCH$_2$CH$_2$CH$_2$NH$_2$, —NHCH$_2$CH$_2$NHCH$_2$CH$_2$CH$_2$NHCH$_2$CH$_2$CH$_2$NH$_2$, or —NHCH$_2$CH$_2$NH(CH$_2$CH$_2$NH)$_d$CH$_2$CH$_2$NH$_2$, where d is from 0 to 50.

In one aspect, the amine-modified natural polymer can include an aryl group having one or more amino groups directly or indirectly attached to the aromatic group. Alternatively, the amino group can be incorporated in the aromatic ring. For example, the aromatic amino group is a pyrrole, an isopyrrole, a pyrazole, imidazole, a triazole, or an indole. In another aspect, the aromatic amino group includes the isoimidazole group present in histidine. In another aspect, the biodegradable polyamine can be gelatin modified with ethylenediamine.

In another aspect, the polycation can be a micelle or mixed micelle formed with cationic surfactants. The cationic surfactant can be mixed with nonionic surfactants to create micelles with variable charge ratios. The micelles are polycationic by virtue of the hydrophobic interactions that form a polyvalent micelle.

Examples of nonionic surfactants include the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles, most preferably about 5 to about 20 moles of ethylene oxide. Examples of such nonionic ethoxylated fatty alcohol surfactants are the Tergitol™ 15-S series from Union Carbide and Brij™ surfactants from ICI. Tergitol™ 15-S Surfactants include $C_{11}$-$C_{15}$ secondary alcohol polyethyleneglycol ethers. Brij™97 surfactant is polyoxyethylene(10) oleyl ether; Brij™58 surfactant is polyoxyethylene (20) cetyl ether; and Brij™ 76 surfactant is polyoxyethylene (10) stearyl ether.

Another useful class of nonionic surfactants include the polyethylene oxide condensates of one mole of alkyl phenol containing from about 6 to 12 carbon atoms in a straight or branched chain configuration, with ethylene oxide. Examples of nonreactive nonionic surfactants are the Igepal™ CO and CA series from Rhone-Poulenc. Igepal™CO surfactants include nonylphenoxy poly(ethyleneoxy)ethanols. Igepal™ CA surfactants include octylphenoxy poly(ethyleneoxy)ethanols.

Another useful class of hydrocarbon nonionic surfactants include block copolymers of ethylene oxide and propylene oxide or butylene oxide. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers.

In other aspects, the nonionic surfactants include sorbitan fatty acid esters, polyoxyethylene sorbitan fatty acid esters and polyoxyethylene stearates. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates.

In one aspect, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Examples of cationic surfactants useful for making cationic micelles include alkylamine salts, quaternary ammonium salts, sulphonium salts, and phosphonium salts. Non-limiting examples of cationic surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, specifically amido propyldimethyl amine (APA).

In one aspect, the polycation includes a polyacrylate having one or more pendant amino groups. For example, the backbone of the polycation can be derived from the polymerization of acrylate monomers including, but not limited to, acrylates, methacrylates, acrylamides, and the like. In one aspect, the polycation backbone is derived from polyacrylamide. In other aspects, the polycation is a block co-polymer, where segments or portions of the co-polymer possess cationic groups or neutral groups depending upon the selection of the monomers used to produce the co-polymer.

Figure 4:
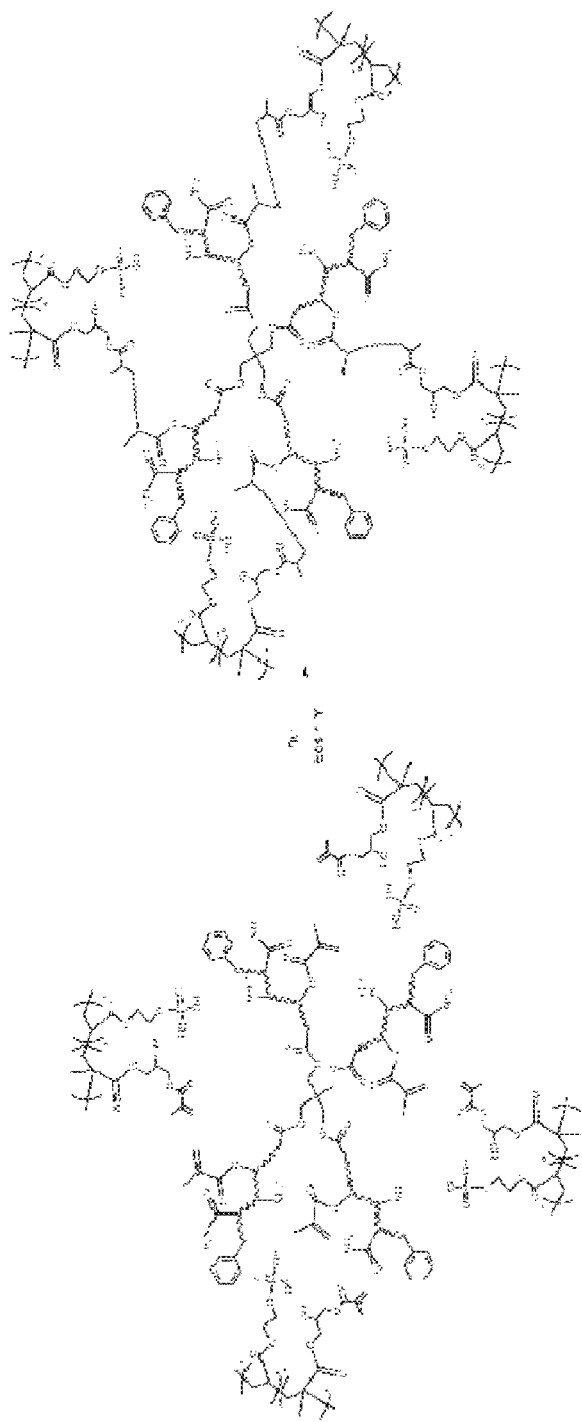
FIG. 4 shows the photocrosslinking of complex coacervates. The polyamine and polyphosphate that form the complex coacervates through electrostatic interactions have methacrylate sidechains that covalently crosslink in the presence of an initiator (e.g., irradiated in the presence of a photoinitiator such as eosin Y.

In other aspects, the polycation can be a dendrimer. The dendrimer can be a branched polymer, a multi-armed polymer, a star polymer, and the like. In one aspect, the dendrimer is a polyalkylimine dendrimer, a mixed amino/ether dendrimer, a mixed amino/amide dendrimer, or an amino acid dendrimer. In another aspect, the dendrimer is poly (amidoamine), or PAMAM. FIG. 4 depicts an example of a branched polyamine. In this aspect, the polyamine has four arms with pendant free amino groups as well as methacrylate groups (i.e., crosslinkable groups).

In one aspect, the polycation is a polyamino compound. In another aspect, the polyamino compound has 10 to 90 mole % primary amino groups. In a further aspect, the polycation polymer has at least one fragment of the formula I

Figure 2:
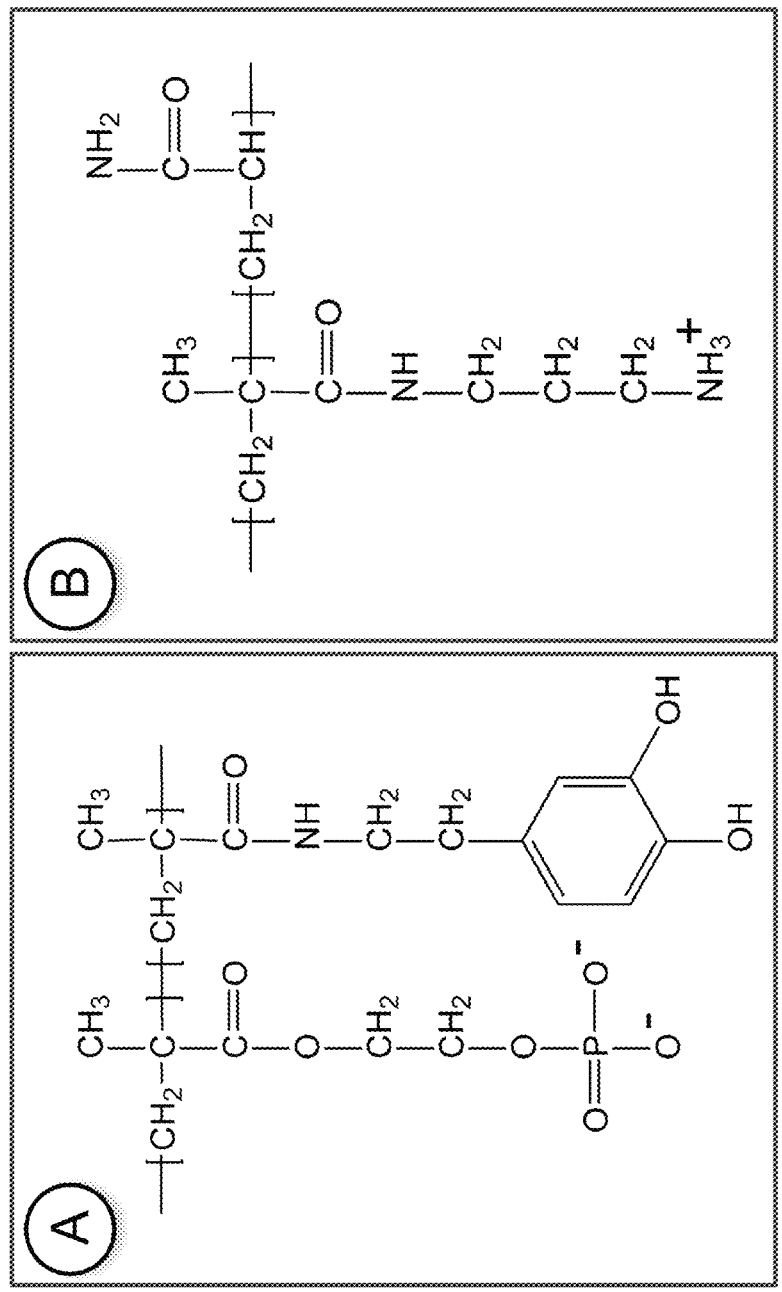
FIG. 2 shows representative synthetic polyanions (A) and polycations (B) used to form adhesive complex coacervates. (A) Polymethacrylate with phosphate and ortho-dihydroxyphenyl sidechains. The phosphate and catecholic groups are both adhesion promoters. (B) Polyacrylamide copolymer with amino-propyl sidechains. These copolymers were used to form the adhesive complex coacervates as shown in FIG. 1.
Figure 3:
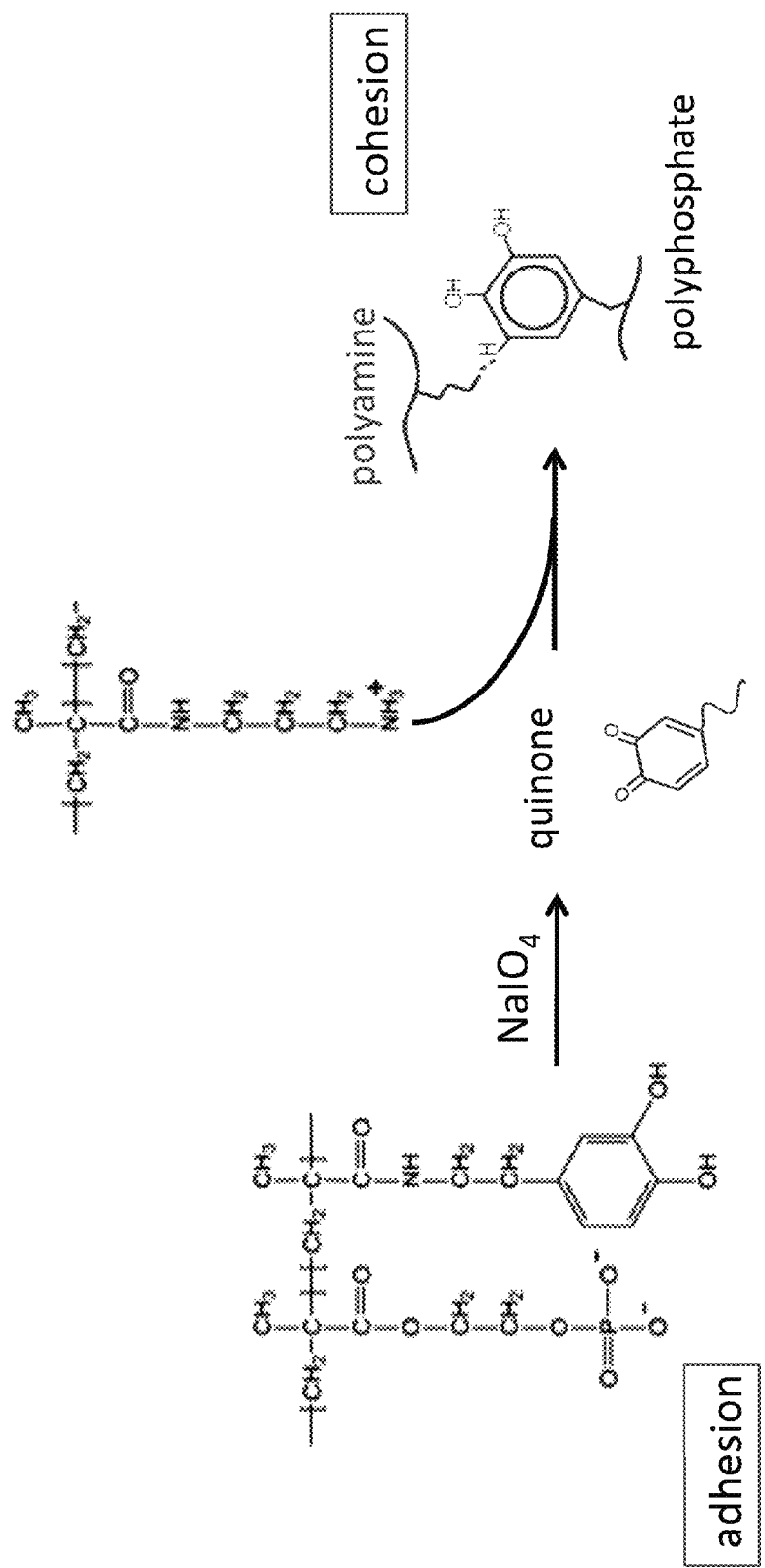
FIG. 3 shows covalent crosslinking between the polycation and polyanion in the adhesive complex coacervate after application of the coacervate to a substrate or pair of substrates to provide cohesive strength. Oxidative crosslinking between a catechol sidechain and a primary amine sidechain is a representative example of a covalent crosslinking method for the polymers in FIG. 2. The crosslinking is initiated by the addition of sodium periodate, which may or may not be complexed with a sugar molecule to control the kinetics of the oxidation reaction. The reaction proceeds through a quinone intermediate that reacts rapidly with nucleophilic groups to form covalent adducts.

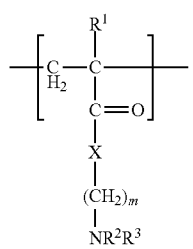

wherein $R^1$, $R^2$, and $R^3$ are, independently, hydrogen or an alkyl group, X is oxygen or $NR^5$, where $R^5$ is hydrogen or an alkyl group, and m is from 1 to 10, or the pharmaceutically-acceptable salt thereof. In another aspect, $R^1$, $R^2$, and $R^3$ are methyl and m is 2. Referring to formula I, the polymer backbone is composed of $CH_2$—$CR^1$ units with pendant —$C(O)X(CH_2)_m NR^2R^3$ units. FIG. 2B show examples of a polycation having the fragment of formula I, where the polymer backbone is derived from methacrylate residues as discussed above. In one aspect, the polycation is the free radical polymerization product of a cationic primary amine monomer (3-amino-propyl methacrylate) and acrylamide, where the molecular weight is from 10 to 200 kd and possesses primary monomer concentrations from 5 to 90 mol %.

II. Polyanions

Similar to the polycation, the polyanion can be a synthetic polymer or naturally-occurring. Examples of other naturally-occurring polyanions include glycosaminoglycans such as condroitin sulfate, heparin, heparin sulfate, dermatan sulfate, and hyaluronic acid. In other aspects, the acidic proteins having a net negative charge at neutral pH or proteins with a low pI can be used as naturally-occurring polyanions described herein. The anionic groups can be pendant to the polymer backbone and/or incorporated in the polymer backbone.

When the polyanion is a synthetic polymer, it is generally any polymer possessing anionic groups or groups that can be readily converted to anionic groups by adjusting the pH. Examples of groups that can be converted to anionic groups include, but are not limited to, carboxylate, sulfonate, phosphonate, boronate, sulfate, borate, or phosphate. Any cationic counterions can be used in association with the anionic polymers if the considerations discussed above are met.

In one aspect, the polyanion is a polyphosphate. In another aspect, the polyanion is a polyphosphate compound having from 5 to 90 mole % phosphate groups. For example, the polyphosphate can be a naturally-occurring compound such as, for example, highly phosphorylated proteins like phosvitin (an egg protein), dentin (a natural tooth phosphoprotein), casein (a phosphorylated milk protein), or bone proteins (e.g. osteopontin).

Alternatively, the polyphosphoserine can be a synthetic polypeptide made by polymerizing the amino acid serine and then chemically phosphorylating the polypeptide. In another aspect, the polyphosphoserine can be produced by the polymerization of phosphoserine. In one aspect, the polyphosphate can be produced by chemically or enzymatically phosphorylating a protein (e.g., natural serine- or threonine-rich proteins). In a further aspect, the polyphosphate can be produced by chemically phosphorylating a polyalcohol including, but not limited to, polysaccharides such as cellulose or dextran.

In another aspect, the polyphosphate can be a synthetic compound. For example, the polyphosphate can be a polymer with pendant phosphate groups attached to the polymer backbone and/or present in the polymer backbone. (e.g., a phosphodiester backbone).

In another aspect, the polyanion can be a micelle or mixed micelle formed with anionic surfactants. The anionic surfactant can be mixed with any of the nonionic surfactants described above to create micelles with variable charge ratios. The micelles are polyanionic by virtue of the hydrophobic interactions that form a polyvalent micelle.

Other useful anionic surfactants include, but are not limited to, alkali metal and (alkyl)ammonium salts of: 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 5) glycinates such as alkyl sarcosinates and alkyl glycinates; 6) sulfosuccinates including dialkyl sulfosuccinates; 7) isothionate derivatives; 8) N-acyltaurine derivatives such as sodium N methyl-N-oleyltaurate); 9) amine oxides including alkyl and alkylamidoalkyldialkylamine oxides; and 10)

alkyl phosphate mono or di-esters such as ethoxylated dodecyl alcohol phosphate ester, sodium salt.

Representative commercial examples of suitable anionic sulfonate surfactants include, for example, sodium lauryl sulfate, available as TEXAPON™ L-100 from Henkel Inc., Wilmington, Del., or as POLYSTEP™ B-3 from Stepan Chemical Co, Northfield, Ill.; sodium 25 lauryl ether sulfate, available as POLYSTEP™ B-12 from Stepan Chemical Co., Northfield, Ill.; ammonium lauryl sulfate, available as STANDAPOL™ A from Henkel Inc., Wilmington, Del.; and sodium dodecyl benzene sulfonate, available as SIPONATE™ DS-10 from Rhone-Poulenc, Inc., Cranberry, N.J., dialkyl sulfosuccinates, having the tradename AEROSOL™ OT, commercially available from Cytec Industries, West Paterson, N.J.; sodium methyl taurate (available under the trade designation NIKKOL™ CMT30 from Nikko Chemicals Co., Tokyo, Japan); secondary alkane sulfonates such as Hostapur™ SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16) fatty acid available from Stepan Company under the trade designation ALPHASTE™ PC48; alkylsulfoacetates and alkylsulfosuccinates available as sodium laurylsulfoacetate (under the trade designation LANTHANOL™ LAL) and disodiumlaurethsulfosuccinate (STEPANMILD™ SL3), both from Stepan Company; alkylsulfates such as ammoniumlauryl sulfate commercially available under the trade designation STEPANOL™ AM from Stepan Company, and or dodecylbenzenesulfonic acid sold under BIO-SOFT® AS-100 from Stepan Chemical Co. In one aspect, the surfactant can be a disodium alpha olefin sulfonate, which contains a mixture of $C_{12}$ to $C_{16}$ sulfonates. In one aspect, CALSOFT™ AOS-40 manufactured by Pilot Corp. can be used herein as the surfactant. In another aspect, the surfactant is DOWFAX 2A1 or 2G manufactured by Dow Chemical, which are alkyl diphenyl oxide disulfonates.

Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™ 340 KL from Clariant Corp., as well as PPG-5 cetyl 10 phosphate available under the trade designation CRODAPHOS™ SG from Croda Inc., Parsipanny, N.J.

Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In other aspects, phosphorous containing polymers, for example, a phospholipid, can be converted into a polyanions. For example, a phospholipid or phosphosugar can be converted into a polyanion to produce a liposome or micelle. Thus, in this aspect, the complex coacervate is a charged hydrophobically associated colloid.

In one aspect, the polyanion includes a polyacrylate having one or more pendant phosphate groups. For example, the polyanion can be derived from the polymerization of acrylate monomers including, but not limited to, acrylates, methacrylates, and the like. In other aspects, the polyanion is a block co-polymer, where segments or portions of the co-polymer possess anionic groups and neutral groups depending upon the selection of the monomers used to produce the co-polymer.

In another aspect, the polyanion is a polymer having at least one fragment having the formula X

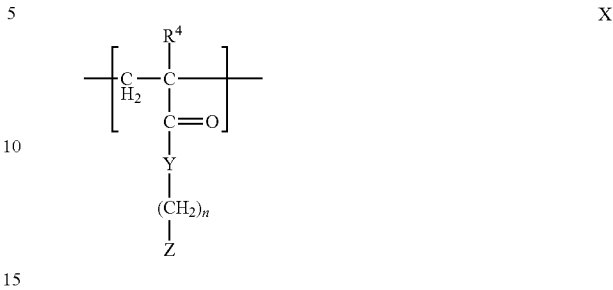

wherein $R^4$ is hydrogen or an alkyl group;
n is from 1 to 10;
Y is oxygen, sulfur, or $NR^{30}$, wherein $R^{30}$ is hydrogen, an alkyl group, or an aryl group;
Z is an anionic group or a group that can be converted to an anionic group, or the pharmaceutically-acceptable salt thereof.

In one aspect, Z in formula X is sulfate, sulfonate, carboxylate, borate, boronate, a substituted or unsubstituted phosphate, or a phosphonate.

In another aspect, the polyanion is a polymer having at least one fragment having the formula II

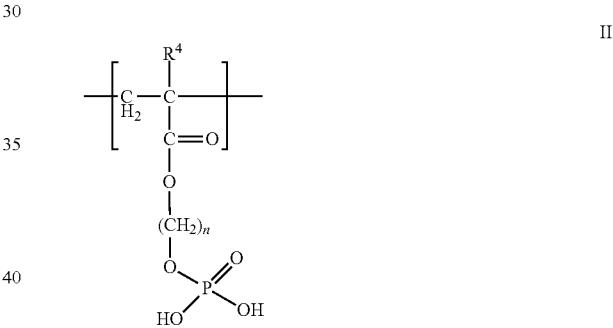

wherein $R^4$ is hydrogen or an alkyl group, and n is from 1 to 10, or the pharmaceutically-acceptable salt thereof. In another aspect, wherein $R^4$ is methyl and n is 2. FIG. 2A shows an example of a polyanion useful herein that has the fragment of formula II, where the polymer backbone is derived from methacrylate residues. In one aspect, the polyanion is the copolymerization product of methacryloxyethyl phosphate and acrylamide, where the mass average molecular weight is from 10,000 to 200,000, preferably 50,000, and has phosphate groups in the amount of 20 to 90 mol %.

III. Crosslinkable Groups

In certain aspects, the polycations and polyanions can contain groups that permit crosslinking between the two polymers upon curing to produce new covalent bonds. The mechanism of crosslinking can vary depending upon the selection of the crosslinking groups. In one aspect, the crosslinking groups can be electrophiles and nucleophiles. For example, the polyanion can have one or more electrophilic groups, and the polycations can have one or more nucleophilic groups capable of reacting with the electrophilic groups to produce new covalent bonds. Examples of electrophilic groups include, but are not limited to, anhydride groups, esters, ketones, lactams (e.g., maleimides and succinimides), lactones, epoxide groups, isocyanate groups, and aldehydes. Examples of nucleophilic groups are presented below. In one aspect, the polycation and polyanion can crosslink with one another via a Michael addition. For example, the polycation can have one or more nucleophilic groups such as, for example, a hydroxyl or thiol group that can react with an olefinic group present on the polyanion.

In one aspect, the crosslinking group on the polyanion comprises an olefinic group and the crosslinking group on the polycation comprises a nucleophilic group that reacts with the olefinic group to produce a new covalent bond. In another aspect, the crosslinking group on the polycation comprises an olefinic group and the crosslinking group on the polyanion comprises a nucleophilic group that reacts with the olefinic group to produce a new covalent bond.

In another aspect, the polycation and polyanion each have an actinically crosslinkable group (FIG. 4). As used herein, "actinically crosslinkable group" in reference to curing or polymerizing means that the crosslinking between the polycation and polyanion is performed by actinic irradiation, such as, for example, UV irradiation, visible light irradiation, ionized radiation (e.g. gamma ray or X-ray irradiation), microwave irradiation, and the like. Actinic curing methods are well-known to a person skilled in the art. The actinically crosslinkable group can be an unsaturated organic group such as, for example, an olefinic group. Examples of olefinic groups useful herein include, but are not limited to, an acrylate group, a methacrylate group, an acrylamide group, a methacrylamide group, an allyl group, a vinyl group, a vinylester group, or a styrenyl group. In another aspect, the actinically crosslinkable group can be an azido group. For example, crosslinking can occur between the polycation and polyanion via light activated crosslinking through azido groups.

Any of the polymers described above (synthetic or naturally-occurring) that can be used as the polycation and polyanion can be modified to include the actinically crosslinkable group. For example, a polyphosphate can be modified to include the actinically crosslinkable group(s). In one aspect, the polycation and/or polyanion can include at least one fragment having the formula VII

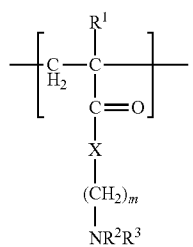

wherein $R^1$, $R^2$, and $R^3$ are, independently, hydrogen or an alkyl group, X is oxygen or $NR^5$, where $R^5$ is hydrogen or an alkyl group, and m is from 1 to 10, or the pharmaceutically-acceptable salt thereof, wherein at least one of $R^2$ or $R^3$ is an actinically crosslinkable group. In one aspect, referring to formula VII, $R^1$ is methyl, $R^2$ is hydrogen, $R^3$ is an acrylate or methacrylate group, X is NH, and m is 2.

In one aspect, the polycation is a polyamino compound modified to include one or more acrylate or methacrylate groups. Any of the polyamino compounds described above that is useful as the polycation can be chemically modified to incorporate one or more acrylate or methacrylate groups. An example of this can be found in FIG. 4, where the branched polyamino compound has a methacrylate groups attached to each arm of the polyamine. The number of acrylate or methacrylate groups attached to the polyamino compound can vary as needed.

In one aspect, the polyanion is a phosphate compound modified to include one or more acrylate or methacrylate groups. Any of the phosphate compounds described above that is useful as the polyanion can be chemically modified to incorporate one or more acrylate or methacrylate groups. An example of this can be found in FIG. 4, where a phosphate compound with a pendant carboxylic acid group was reacted with glycidyl methacrylate to produce the phosphate compound with a terminal methacrylate group. The number of acrylate or methacrylate groups attached to the phosphate compound can vary as needed.

In another aspect, the crosslinkable group includes a dihydroxy-substituted aromatic group capable of undergoing oxidation in the presence of an oxidant (see e.g., FIG. 2A). In one aspect, the dihydroxy-substituted aromatic group is an ortho-dihydroxy aromatic group capable of being oxidized to the corresponding quinone. In another aspect, the dihydroxyl-substituted aromatic group is a dihydroxyphenol or halogenated dihydroxyphenol group such as, for example, DOPA and catechol (3,4 dihydroxyphenol). For example, in the case of DOPA, it can be oxidized to dopaquinone. Dopaquinone is capable of either reacting with a neighboring DOPA group or another nucleophilic group. In the presence of an oxidant such as oxygen or other additives including, but not limited to, peroxides, periodates (e.g., $NaIO_4$), persulfates, permanganates, dichromates, transition metal oxidants (e.g., a $Fe^{+3}$ compound, osmium tetroxide), or enzymes (e.g., catechol oxidase), the dihydroxyl-substituted aromatic group can be oxidized.

In one aspect, the polyanion is the polymerization product between two or more monomers, where one of the monomers has a dihydroxy aromatic group covalently attached to the monomer. For example, the polyanion can be the polymerization product between (1) a phosphate acrylate and/or phosphate methacrylate and (2) a second acrylate and/or second methacrylate having a dihydroxy aromatic group covalently bonded to the second acrylate or second methacrylate. In another aspect, the polyanion is the polymerization product between methacryloxyethyl phosphate and dopamine methacrylamide (FIG. 2A). In each of these polymers, an acrylate containing the pendant ortho-dihydroxyphenyl residue is polymerized with the appropriate monomers to produce the polyanion with pendant ortho-dihydroxyphenyl residues. Oxidation of ortho-dihydroxyphenyl groups results in orthoquinone groups, a reactive intermediate and can crosslink (i.e., react) with nucleophiles such as, for example, amino, hydroxyl, or thiol groups via a Michael-type addition to form a new covalent bond. For example, a lysyl group on the polycation can react with the orthoquinone residue on the polyanion to produce new covalent bonds. Although an ortho-dihydroxyphenyl group is a suitable crosslinking group, other groups such as, for example, tyrosine can be used herein. The importance of crosslinking with respect to the use of the adhesive complex coacervates described herein will be discussed below.

In certain aspects, the oxidant used above can be stabilized. For example, a compound that forms a complex with periodate that is not redox active can result in a stabilized oxidant. In other words, the periodate is stabilized in a non-oxidative form and cannot oxidize the ortho-dihydroxy-substituted aromatic group while in the complex. The complex is reversible and even if it has a very high stability constant there is a small amount of uncomplexed periodate formed. The ortho-dihydroxyl-substituted aromatic group competes with the compound for the small amount of free periodate. As the free periodate is oxidized more is released from the equilibrium complex. In one aspect, sugars possessing a cis,cis-1,2,3-triol grouping on a six-membered ring can form competitive periodate complexes. An example of a specific compound that forms stable periodate complex is 1,2-O-isopropylidene-alpha-D-glucofuranose (A. S. Perlin and E. VON Rudloff, Canadian Journal of Chemistry. Volume 43 (1965)). The stabilized oxidant can control the rate of crosslinking. Not wishing to be bound by theory, the stabilized oxidant slows the rate of oxidation providing time to add the oxidant and position the substrate before the adhesive hardens irreversibly.

In other aspects, the crosslinkers present on the polycation and/or polyanion can form coordination complexes with transition metal ions. For example, a transition metal ion can be added to a mixture of polycation and polyanion, where both polymers contain groups capable of coordinating transition metal ions.

Examples of coordinating sidechains are catechols, imidazoles, phosphates, carboxylic acids, and combinations. The rate of coordination and dissociation can be controlled by the selection of the coordination group, the transition metal ion, and the pH. Thus, in addition to covalent crosslinking as described above, crosslinking can occur through electrostatic, ionic, coordinative, or other non-covalent bonding. Transition metal ions such as, for example, iron, copper, vanadium, zinc, and nickel can be used herein.

In certain aspects, the adhesive complex coacervate can also include a multivalent crosslinker. In one aspect, the multivalent crosslinker has two or more nucleophilic groups (e.g., hydroxyl, thiol, etc.) that react with crosslinkable groups (e.g., olefinic groups) present on the polycation and polyanion via a Michael addition reaction to produce a new covalent bond. In one aspect, the multivalent crosslinker is a di-thiol or tri-thiol compound.

IV. Reinforcing Components

Figure 5:
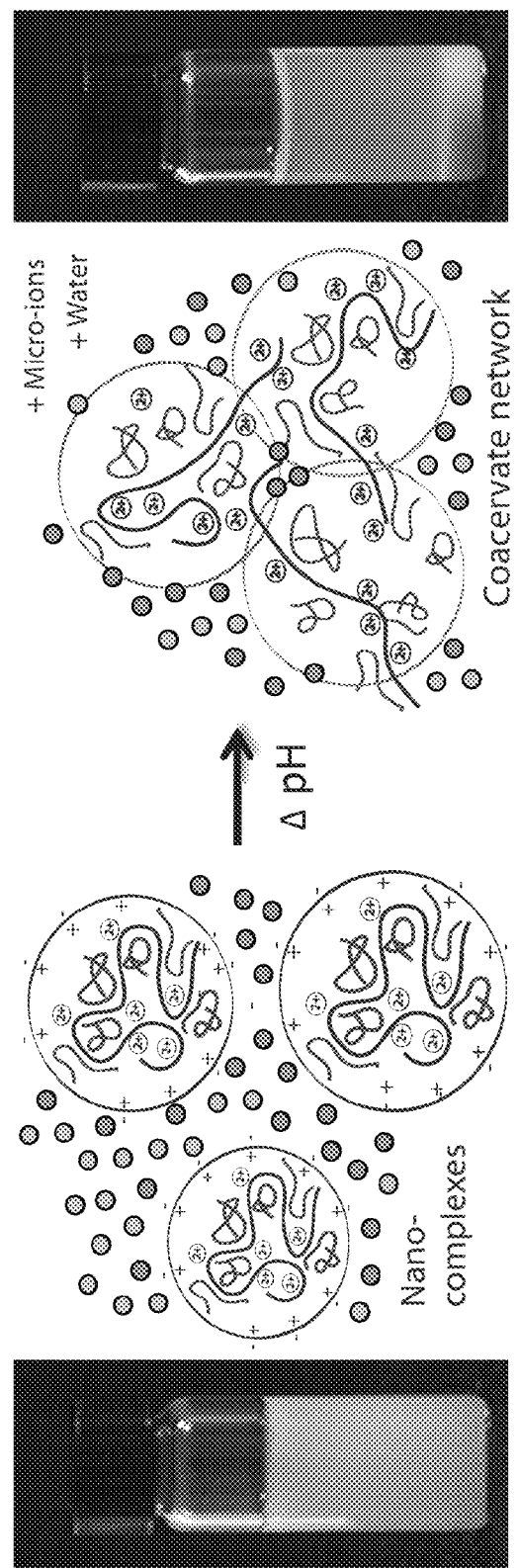
FIG. 5 shows the incorporation of reinforcing components into the adhesive complex coacervates to improve mechanical properties. (Left) Water-soluble, or water-suspendable components, or solid particles present in the solution before the complex coacervate condenses will be entrapped in the watery phase of complex coacervate network (right).

The coacervates described herein include a reinforcing component. The term "reinforcing component" is defined herein as any component that enhances or improves the mechanical properties (e.g., cohesiveness, fracture toughness, elastic modulus, the ability to release and bioactive agents, dimensional stability after curing, etc.) of the adhesive complex coacervate prior to or after the curing of the coacervate when compared to the same coacervate that does not include the reinforcing component. The mode in which the reinforcing component can enhance the mechanical properties of the coacervate can vary, and will depend upon the intended application of the adhesives as well as the selection of the polycation, polyanion, and reinforcing component. For example, upon curing the coacervate, the polycations and/or polyanions present in the coacervate can covalently crosslink with the reinforcing component. In other aspects, the reinforcing component can occupy a space or "phase" in the coacervate, which ultimately increases the mechanical properties of the coacervate. Examples of reinforcing components useful herein are provided below. FIG. 5 shows the incorporation of water soluble or water-suspendable particles in the adhesive complex coacervate.

In one aspect, the reinforcing component is a polymerizable monomer. The polymerizable monomer entrapped in the complex coacervate can be any water soluble monomer capable of undergoing polymerization in order to produce an interpenetrating polymer network. The selection of the polymerizable monomer can vary depending upon the application. Factors such as molecular weight can be altered to modify the solubility properties of the polymerizable monomer in water as well as the mechanical properties of the resulting coacervate, The selection of the functional group on the polymerizable monomer determines the mode of polymerization. For example, the polymerizable monomer can be a polymerizable olefinic monomer that can undergo polymerization through mechanisms such as, for example, free radical polymerization and Michael addition reactions. In one aspect, the polymerizable monomer has two or more olefinic groups. In one aspect, the monomer comprises one or two actinically crosslinkable groups. As discussed above, "actinically crosslinkable group" in reference to curing or polymerizing means that the crosslinking between the polymerizable monomer is performed by actinic irradiation, such as, for example, UV irradiation, visible light irradiation, ionized radiation (e.g. gamma ray or X-ray irradiation), microwave irradiation, and the like. This can be performed in the presence of a photoinitiator, which is discussed in detail below. Actinic curing methods are well-known to a person skilled in the art. Examples of actinically crosslinkable group useful herein include, but are not limited to, a pendant acrylate group, methacrylate group, acrylamide group, methacrylamide group, allyl, vinyl group, vinylester group, or styrenyl group. Alternatively, polymerization can be performed in the presence of an initiator and coinitiator which are also discussed in detail below.

Examples of water-soluble polymerizable monomers include, but are not limited to, hydroxyalkyl methacrylate (HEMA), hydroxyalkyl acrylate, N-vinyl pyrrolidone, N-methyl-3-methylidene-pyrrolidone, allyl alcohol, N-vinyl alkylamide, N-vinyl-N-alkylamide, acrylamides, methacrylamide, (lower alkyl)acrylamides and methacrylamides, and hydroxyl-substituted (lower alkyl)acrylamides and -methacrylamides. In one aspect, the polymerizable monomer is a diacrylate compound or dimethacrylate compound. In another aspect, the polymerizable monomer is a polyalkylene oxide glycol diacrylate or dimethacrylate. For example, the polyalkylene can be a polymer of ethylene glycol, propylene glycol, or block co-polymers thereof. In one aspect, the polymerizable monomer is polyethylene glycol diacrylate or polyethylene glycol dimethacrylate. In one aspect, the polyethylene glycol diacrylate or polyethylene glycol dimethacrylate has a $M_n$ of 200 to 2,000, 400 to 1,500, 500 to 1,000, 500 to 750, or 500 to 600.

In another aspect, the reinforcing component can be a nanostructure. Depending upon the selection of the nanostructure, the polycation and/or polyanion can be covalently crosslinked to the nanostructure. Alternatively, the nanostructures can be physically entrapped within the coacervate. Nanostructures can include, for example, nanotubes, nanowires, nanorods, or a combination thereof. In the case of nanotubes, nanowires, and nanorods, one of the dimensions of the nanostructure is less than 100 nm.

The nanostructures useful herein can be composed of organic and/or inorganic materials. In one aspect, the nanostructures can be composed of organic materials like carbon or inorganic materials including, but not limited to, boron, molybdenum, tungsten, silicon, titanium, copper, bismuth, tungsten carbide, aluminum oxide, titanium dioxide, molybdenum disulphide, silicon carbide, titanium diboride, boron nitride, dysprosium oxide, iron (III) oxide-hydroxide, iron oxide, manganese oxide, titanium dioxide, boron carbide, aluminum nitride, or any combination thereof.

In certain aspects, the nanostructures can be functionalized in order to react (i.e., crosslink) with the polycation and/or polyanion. For example, carbon nanotubes can be functionalized with —OH or —COOH groups. In other aspects, it is desirable to use two or more different types of nanostructures. For example, a carbon nanostructure can be used in combination with one or more inorganic nanostructures.

In other aspects, the reinforcing component can be a water-insoluble filler. The filler can have a variety of different sizes and shapes, ranging from particles to fibrous materials. In one aspect, the filler is a nano-sized particle. Compared to micron-sized silica fillers, nanoscale fillers have several desirable properties. First, the higher specific surface area of nano- vs. microparticles increases the stress transfer from the polymer matrix to the rigid filler. Second, smaller volumes of nanofiller are required than of the larger micron-sized particles for a greater increase in toughness. Additionally, an important consequence of the smaller diameters and lower fill volumes of nanoparticles is reduced viscosity of the uncured adhesive, which has direct benefits for processability. This is advantageous, as the coacervate can retain its injectable character while potentially increasing bond strengths dramatically. Third, maximum toughening requires uniform dispersion of the filler particles within the coacervate. Nanoscale colloidal particles, again because of the small diameter, lend themselves more readily to stable dispersions within the coacervate.

In one aspect, the filler comprises a metal oxide, a ceramic particle, or a water insoluble inorganic salt. Examples of the nanoparticles or nanopowders useful herein include those manufactured by SkySpring Nanomaterials, Inc., which is listed below.

Metals and Non-Metal Elements
Ag, 99.95%, 100 nm
Ag, 99.95%, 20-30 nm
Ag, 99.95%, 20-30 nm, PVP coated
Ag, 99.9%, 50-60 nm
Ag, 99.99%, 30-50 nm, oleic acid coated
Ag, 99.99%, 15 nm, 10 wt %, self-dispersible
Ag, 99.99%, 15 nm, 25 wt %, self-dispersible
Al, 99.9%, 18 nm
Al, 99.9%, 40-60 nm
Al, 99.9%, 60-80 nm
Al, 99.9%, 40-60 nm, low oxygen
Au, 99.9%, 100 nm
Au, 99.99%, 15 nm, 10 wt %, self-dispersible
B, 99.9999%
B, 99.999%
B, 99.99%
B, 99.9%
B, 99.9%, 80 nm
Diamond, 95%, 3-4 nm
Diamond, 93%, 3-4 nm
Diamond, 55-75%, 4-15 nm
Graphite, 93%, 3-4 nm
Super Activated Carbon, 100 nm
Co, 99.8%, 25-30 nm
Cr, 99.9%, 60-80 nm
Cu, 99.5%, 300 nm
Cu, 99.5%, 500 nm
Cu, 99.9%, 25 nm
Cu, 99.9%, 40-60 nm
Cu, 99.9%, 60-80 nm
Cu, 5-7 nm, dispersion, oil soluble
Fe, 99.9%, 20 nm
Fe, 99.9%, 40-60 nm
Fe, 99.9%, 60-80 nm
Carbonyl-Fe, micro-sized
Mo, 99.9%, 60-80 nm
Mo, 99.9%, 0.5-0.8 nm
Ni, 99.9%, 500 nm (adjustable)
Ni, 99.9%, 20 nm
Ni coated with carbon, 99.9%, 20 nm
Ni, 99.9%, 40-60 nm
Ni, 99.9%, 60-80 nm
Carbonyl-Ni, 2-3 nm
Carbonyl-Ni, 4-7 nm
Carbonyl-Ni—Al (Ni Shell, Al Core)
Carbonyl-Ni—Fe Alloy
Pt, 99.95%, 5 nm, 10 wt %, self-dispersible
Si, Cubic, 99%, 50 nm
Si, Polycrystalline, 99.99995%, lumps
Sn, 99.9%, <100 nm
Ta, 99.9%, 60-80 nm
Ti, 99.9%, 40-60 nm
Ti, 99.9%, 60-80 nm
W, 99.9%, 40-60 nm
W, 99.9%, 80-100 nm
Zn, 99.9%, 40-60 nm
Zn, 99.9%, 80-100 nm
Metal Oxides
AlOOH, 10-20 nm, 99.99%
$Al_2O_3$ alpha, 98+%, 40 nm
$Al_2O_3$ alpha, 99.999%, 0.5-10 μm
$Al_2O_3$ alpha, 99.99%, 50 nm
$Al_2O_3$ alpha, 99.99%, 0.3-0.8 μm
$Al_2O_3$ alpha, 99.99%, 0.8-1.5 μm
$Al_2O_3$ alpha, 99.99%, 1.5-3.5 μm
$Al_2O_3$ alpha, 99.99%, 3.5-15 μm
$Al_2O_3$ gamma, 99.9%, 5 nm
$Al_2O_3$ gamma, 99.99%, 20 nm
$Al_2O_3$ gamma, 99.99%, 0.4-1.5 μm
$Al_2O_3$ gamma, 99.99%, 3-10 μm
$Al_2O_3$ gamma, Extrudate
$Al_2O_3$ gamma, Extrudate
$Al(OH)_3$, 99.99%, 30-100 nm
$Al(OH)_3$, 99.99%, 2-10 μm
Aluminium Iso-Propoxide (AIP), $C_9H_{21}O_3Al$, 99.9%
AlN, 99%, 40 nm
BaTiO3, 99.9%, 100 nm
$BBr_3$, 99.9%
$B_2O_3$, 99.5%, 80 nm
BN, 99.99%, 3-4 μm
BN, 99.9%, 3-4 μm
$B_4C$, 99%, 50 nm
$Bi_2O_3$, 99.9%, <200 nm
$CaCO_3$, 97.5%, 15-40 nm
$CaCO_3$, 15-40 nm
$Ca_3(PO_4)_2$, 20-40 nm
$Ca_{10}(PO_4)_6(OH)_2$, 98.5%, 40 nm
$CeO_2$, 99.9%, 10-30 nm
CoO, <100 nm
$Co_2O_3$, <100 nm
$Co_3O_4$, 50 nm
CuO, 99+%, 40 nm
$Er_2O_3$, 99.9%, 40-50 nm
$Fe_2O_3$ alpha, 99%, 20-40 nm
$Fe_2O_3$ gamma, 99%, 20-40 nm
$Fe_3O_4$, 98+%, 20-30 nm
$Fe_3O_4$, 98+%, 10-20 nm
$Gd_2O_3$, 99.9%<100 nm
$HfO_2$, 99.9%, 100 nm
$In_2O_3:SnO_2=90:10$, 20-70 nm
$In_2O_3$, 99.99%, 20-70 nm
$In(OH)_3$, 99.99%, 20-70 nm LaB$_6$, 99.0%, 50-80 nm
La$_2$O$_3$, 99.99%, 100 nm
LiFePO$_4$, 40 nm
MgO, 99.9%, 10-30 nm
MgO, 99%, 20 nm
MgO, 99.9%, 10-30 nm
Mg(OH)$_2$, 99.8%, 50 nm
Mn$_2$O$_3$, 98+%, 40-60 nm
MoCl$_5$, 99.0%
Nd$_2$O$_3$, 99.9%, <100 nm
NiO, <100 nm
Ni$_2$O$_3$, <100 nm
Sb$_2$O$_3$, 99.9%, 150 nm
SiO$_2$, 99.9%, 20-60 nm
SiO$_2$, 99%, 10-30 nm, treated with Silane Coupling Agents
SiO$_2$, 99%, 10-30 nm, treated with Hexamethyldisilazane
SiO$_2$, 99%, 10-30 nm, treated with Titanium Ester
SiO$_2$, 99%, 10-30 nm, treated with Silanes
SiO$_2$, 10-20 nm, modified with amino group, dispersible
SiO$_2$, 10-20 nm, modified with epoxy group, dispersible
SiO$_2$, 10-20 nm, modified with double bond, dispersible
SiO$_2$, 10-20 nm, surface modified with double layer, dispersible
SiO$_2$, 10-20 nm, surface modified, super-hydrophobic & oleophilic, dispersible
SiO$_2$, 99.8%, 5-15 nm, surface modified, hydrophobic & oleophilic, dispersible
SiO$_2$, 99.8%, 10-25 nm, surface modified, super-hydrophobic, dispersible
SiC, beta, 99%, 40 nm
SiC, beta, whisker, 99.9%
Si$_3$N$_4$, amorphous, 99%, 20 nm
Si$_3$N$_4$ alpha, 97.5-99%, fiber, 100 nm×800 nm
SnO$_2$, 99.9%, 50-70 nm
ATO, SnO$_2$:Sb$_2$O$_3$=90:10, 40 nm
TiO$_2$ anatase, 99.5%, 5-10 nm
TiO$_2$ Rutile, 99.5%, 10-30 nm
TiO$_2$ Rutile, 99%, 20-40 nm, coated with SiO$_2$, highly hydrophobic
TiO$_2$ Rutile, 99%, 20-40 nm, coated with SiO$_2$/Al$_2$O$_3$
TiO$_2$ Rutile, 99%, 20-40 nm, coated with Al$_2$O$_3$, hydrophilic
TiO$_2$ Rutile, 99%, 20-40 nm, coated with SiO$_2$/Al$_2$O$_3$/Stearic Acid
TiO$_2$ Rutile, 99%, 20-40 nm, coated with Silicone Oil, hydrophobic
TiC, 99%, 40 nm
TiN, 97+%, 20 nm
WO$_3$, 99.5%, <100 nm
WS$_2$, 99.9%, 0.8 μm
WCl$_6$, 99.0%
Y$_2$O$_3$, 99.995%, 30-50 nm
ZnO, 99.8%, 10-30 nm
ZnO, 99%, 10-30 nm, treated with silane coupling agents
ZnO, 99%, 10-30 nm, treated with stearic acid
ZnO, 99%, 10-30 nm, treated with silicone oil
ZnO, 99.8%, 200 nm
ZrO$_2$, 99.9%, 100 nm
ZrO$_2$, 99.9%, 20-30 nm
ZrO$_2$-3Y, 99.9%, 0.3-0.5 um
ZrO$_2$-3Y, 25 nm
ZrO$_2$-5Y, 20-30 nm
ZrO$_2$-8Y, 99.9%, 0.3-0.5 μm
ZrO$_2$-8Y, 20 nm
ZrC, 97+%, 60 nm In one aspect, the filler is nanosilica. Nanosilica is commercially available from multiple sources in a broad size range. For example, aqueous Nexsil colloidal silica is available in diameters from 6-85 nm from Nyacol Nanotechnologies, Inc. Amino-modified nanosilica is also commercially available, from Sigma Aldrich for example, but in a narrower range of diameters than unmodified silica. Nanosilica does not contribute to the opacity of the coacervate, which is an important attribute of the adhesives and glues produced therefrom.

In another aspect, the filler can be composed of calcium phosphate. In one aspect, the filler can be hydroxyapatite, which has the formula Ca$_5$(PO$_4$)$_3$OH. In another aspect, the filler can be a substituted hydroxyapatite. A substituted hydroxyapatite is hydroxyapatite with one or more atoms substituted with another atom. The substituted hydroxyapatite is depicted by the formula M$_5$X$_3$Y, where M is Ca, Mg, Na; X is PO$_4$ or CO$_3$; and Y is OH, F, Cl, or CO$_3$. Minor impurities in the hydroxyapatite structure may also be present from the following ions: Zn, Sr, Al, Pb, Ba. In another aspect, the calcium phosphate comprises a calcium orthophosphate. Examples of calcium orthophosphates include, but are not limited to, monocalcium phosphate anhydrate, monocalcium phosphate monohydrate, dicalcium phosphate dihydrate, dicalcium phosphate anhydrous, octacalcium phosphate, beta tricalcium phosphate, alpha tricalcium phosphate, super alpha tricalcium phosphate, tetracalcium phosphate, amorphous tricalcium phosphate, or any combination thereof. In other aspects, the calcium phosphate can also include calcium-deficient hydroxyapatite, which can preferentially adsorb bone matrix proteins.

In certain aspects, the filler can be functionalized with one or more polymerizable functional groups that are capable of capable of reacting with a crosslinkable group on the polycation and/or polyanion and, when present the polymerizable monomer. In this aspect, the filler is covalently attached to the polycation and/or polyanion and, when present, the interpenetrating network. For example, aminated silica can be reacted with a compound that possesses (1) a functional group capable of reacting with the amino groups present on the silica and (2) an olefinic group capable of undergoing polymerization. Thus, the olefinic groups are covalently attached to the silica. In one aspect, aminated nanosilica can be reacted with acryloyl chloride to covalently attach an acrylate group to the silica. Depending upon the selection of the polycation and polyanion, the filler can react with these components to covalently attach to the complex coacervate and, when present, interpenetrating network.

In another aspect, the filler includes one or more nucleophilic groups capable of reacting with a crosslinkable group on the polycation and/or polyanion and, when present, the polymerizable monomer. For example, the filler particle can be modified with surface amines or thiols (i.e., nucleophiles) that can react with react with electrophiles (e.g., orthoquiniones produced by the oxidizing o-dihydroxyphenyl groups) in the coacervate polymer network. In other aspects, nucleophilic groups present on the filler can react with olefinic groups present in the polymerizable monomer and/or coacervate polymer network via a Michael addition reaction.

In other aspects, the filler can be modified to produce charged groups such that the filler can form electrostatic bonds with the coacervate polymer network and/or the interpenetrating network when a polymerizable monomer is used. For example, aminated silica can be added to a solution and the pH adjusted so that the amino groups are protonated and available for electrostatic bonding.

In one aspect, the reinforcing component can be micelles or liposomes. In general, the micelles and liposomes used in this aspect are different from the micelles or liposomes used as polycations and polyanions for preparing the coacervate. The micelles and liposomes can be prepared from the nonionic, cationic, or anionic surfactants described above. The charge of the micelles and liposomes can vary depending upon the selection of the polycation or polyanion as well as the intended use of the coacervate. In one aspect, the micelles and liposomes can be used to solubilize hydrophobic compounds such pharmaceutical compounds. Thus, in addition to be used as adhesives, the reinforced adhesive complex coacervates described herein can be effective as a bioactive delivery device.

V. Initiators and Other Components

In certain aspects, the coacervate also includes one or more initiators entrapped in the coacervate. Examples of initiators useful herein include a thermal initiator, a chemical initiator, or a photoinitiator. In one aspect, when the coacervate includes a polymerizable monomer as the reinforcing component, when the initiator is activated, polymerization of the polymerizable monomer entrapped in the coacervate occurs to produce the interpenetrating network. Additionally, crosslinking can occur between the polycation and polyanion as well as with the interpenetrating network.

Examples of photoinitiators include, but are not limited to a phosphine oxide, a peroxide group, an azide group, an α-hydroxyketone, or an α-aminoketone. In one aspect, the photoinitiator includes, but is not limited to, camphorquinone, benzoin methyl ether, 1-hydroxycyclohexylphenyl ketone, or Darocure® or Irgacure® types, for example Darocure® 1173 or Irgacure® 2959. The photoinitiators disclosed in European Patent No. 0632329, which are incorporated by reference, can be used herein. In other aspects, the photoinitiator is a water-soluble photoinitiator including, but not limited to, riboflavin, eosin, eosin y, and rose Bengal.

In one aspect, the initiator has a positively charged functional group. Examples include 2,2'-azobis[2-(5-methyl-2-imidazolin-2-yl)propane]-dihydrochloride; 2,2'-azobis[2-(2-imidazolin-2-yl) propane]dihydrochloride; 2,2'-azobis[2-(2-imidazo-lin-2-yl)propane]disulfate dehydrate; 2,2'-azobis(2-methylpropionamidine)dihydrochloride; 2,2'-azobis[2-(3,4,5,6-tetrahydropyrimidin-2-yl)propane]dihydrochloride; azobis{2-[1-(2-hydroxyethyl)-2-imidazolin-2-yl]propane}dihydrochloride; 2,2'-azobis(1-imino-1-pyrrolidino-2-ethylpropane)dihydrochloride and combinations thereof.

In another aspect, the initiator is an oil soluble initiator. In one aspect, the oil soluble initiator includes organic peroxides or azo compounds. Examples of organic peroxides include ketone peroxides, peroxyketals, hydroperoxides, dialkyl peroxides, diacyl peroxides, peroxydicarbonates, peroxyesters, and the like. Some specific non-limiting examples of organic peroxides that can be used as the oil soluble initiator include: lauroyl peroxide, 1,1-bis(t-hexylperoxy)-3,3,5-trimethylcyclohexane, 1,1-bis(t-butylperoxy)-3,3,5-trimethylcyclohexane, t-butylperoxylaurate, t-butylperoxyisopropylmonocarbonate, t-butylperoxy-2-ethylhexylcarbonate, di-t-butylperoxyhexahydroterephthalate, dicumyl peroxide, 2,5-dimethyl-2,5-di(t-butylperoxy)hexane, di-t-butyl peroxide, t-butylperoxy-2-ethylhexanoate, bis(4-t-butylcyclohexyl)peroxydicarbonate, t-amylperoxy-3,5,5-trimethylhexanoate, 1,1-di(t-amylperoxy)-3,3,5-trimethylcyclohexane, benzoylperoxide, t-butylperoxyacetate, and the like.

Some specific non-limiting examples of azo compounds that can be used as the oil soluble initiator include: 2,2'-azobis-isobutyronitrile, 2,2'-azobis-2,4-dimethylvaleronitrile, 1,1'-azobis-1-cyclohexane-carbonitrile, dimethyl-2,2'-azobisisobutyrate, 1,1'-azobis-(1-acetoxy-1-phenylethane), 4,4'-azobis(4-cyanopentanoic acid) and its soluble salts (e.g., sodium, potassium), and the like.

In one aspect, the initiator is a water-soluble initiator including, but not limited to, potassium persulfate, ammonium persulfate, sodium persulfate, and mixtures thereof. In another aspect, the initiator is an oxidation-reduction initiator such as the reaction product of the above-mentioned persulfates and reducing agents such as sodium metabisulfite and sodium bisulfite; and 4,4'-azobis(4-cyanopentanoic acid) and its soluble salts (e.g., sodium, potassium).

In certain aspects, multiple initiators can be used to broaden the absorption profile of the initiator system in order to increase the initiation rate. For example, two different photoinitiators can be employed that are activated by different wavelengths of light. In another aspect, a co-initiator can be used in combination with any of the initiators described herein. In one aspect, the co-initiator is 2-(diethylamino)ethyl acrylate, 2-(dimethylamino)ethyl acrylate, 2-(dimethylamino)ethyl benzoate, 2-(dimethylamino)ethyl methacrylate, 2-ethylhexyl 4-(dimethylamino)benzoate, 3-(dimethylamino)propyl acrylate, 4,4'-bis(diethylamino) benzophenone, or 4-(diethylamino)benzophenone.

In certain aspects, the initiator and/or co-initiator are covalently attached to the polycation and/or polyanion. For example, the initiator and/or co-initiator can be copolymerized with monomers used to make the polycation and/or polyanion. In one aspect, the initiators and co-initiators possess polymerizable olefinic groups such as acrylate and methacrylate groups (e.g., see examples of co-initiators above) that can be copolymerized with monomers described used to make the polycation and polyanion. In another aspect, the initiators can be chemically grafted onto the backbone of the polycation and polyanion. Thus, in these aspects, the photoinitiator and/or co-initiator are covalently attached to the polymer and pendant to the polymer backbone. This approach will simply formulation and possibly enhance storage and stability.

The adhesive complex coacervates can optionally contain one or more multivalent cations (i.e., cations having a charge of +2 or greater). In one aspect, the multivalent cation can be a divalent cation composed of one or more alkaline earth metals. For example, the divalent cation can be a mixture of $Ca^{+2}$ and $Mg^{+2}$. In other aspects, transition metal ions with a charge of +2 or greater can be used as the multivalent cation. The concentration of the multivalent cations can determine the rate and extent of coacervate formation. Not wishing to be bound by theory, weak cohesive forces between particles in the fluid may be mediated by multivalent cations bridging excess negative surface charges. The amount of multivalent cation used herein can vary. In one aspect, the amount is based upon the number of anionic groups and cationic groups present in the polyanion and polycation.

VI. Preparation of Reinforced Adhesive Complex Coacervates

The synthesis of the reinforced adhesive complex coacervates described herein can be performed using a number of techniques and procedures. Exemplary techniques for producing the coacervates with the polymerizable monomer are provided in the Examples. In one aspect, an aqueous solution of polycation is mixed with an aqueous solution of polyanion, where one or both of the solutions contain the polymerizable monomer and other optional components (e.g., fillers, initiators, etc.). In certain aspects, the pH of each solution can be adjusted to a desired pH (e.g., physiological pH) prior to mixing with one another to produce the complex coacervate. Alternatively, after mixing the polycation, polyanion, polymerizable monomer, and optional components, the pH of the resulting solution can be adjusted to produce the complex coacervate. Upon mixing, the adhesive complex coacervate forms a fluid that settles to the bottom of the solution, at which time the supernatant is removed and the complex coacervate is ready for use to produce the adhesive.

After the adhesive complex coacervate, it is subsequently cured to induce crosslinking within the coacervate to produce a cured adhesive complex coacervate. The cured adhesive complex coacervate is also referred to herein as "an adhesive." Depending upon the selection of starting materials, varying degrees of crosslinking can occur throughout the coacervate during curing. In one aspect, the polycations and polyanions can be crosslinked with one another by covalent bonds upon curing. In other aspects, the polycations and/or polyanions can be crosslinked with the reinforcing component.

In one aspect, after the adhesive complex coacervate has been produced and applied to a substrate or adherend it can be converted to a load bearing adhesive bond using techniques known in the art. In one aspect, the adhesive can be produced by the process comprising
(a) providing an adhesive complex coacervate described herein comprising a polymerizable monomer, and
(b) curing the adhesive complex coacervate to polymerize the polymerizable monomer and produce an interpenetrating network.

In this aspect, step (b) involves curing the adhesive complex coacervate in order to polymerize the polymerizable monomer and produce an interpenetrating network throughout the coacervate. In one aspect, the polycations and polyanions can be crosslinked with one another by covalent bonds upon curing. In other aspects, the polycations and/or polyanions can be crosslinked with the interpenetrating network. For example, the polymerizable monomer can possess groups that can covalently crosslink with the polycation and/or polyanion, which enhances the overall mechanical properties of the coacervate.

The method of polymerizing the polymerizable monomer to produce the interpenetrating network can vary depending upon the nature of the polymerizable monomer. For example, if the polymerizable monomer has one or more polymerizable olefinic groups, an initiator and a co-initiator can be incorporated into the coacervate using the method described above, and the coacervate can be exposed to light. Here, the polymerizable monomer polymerizes in the coacervate to produce the interpenetrating network. Any of the initiators and co-initiators described above can be used herein.

In certain aspects, when the polycation and polyanion possess orthogonally crosslinkable groups, the groups can be crosslinked with one another prior to the polymerization of the polymerizable monomer, after the polymerization of the polymerizable monomer, or simultaneously with the polymerization of the polymerizable monomer. For example, using the techniques described above and in the Examples, the coacervate can be contacted with an oxidant such as $O_2$, $NaIO_4$, a peroxide, or a transition metal oxidant in order to facilitate crosslinking. As discussed above, the rate of oxidative crosslinking can be controlled when the oxidant is combined with certain sugars. This is an important feature, as it may be desirable in certain applications to delay crosslinking.

Figure 6:
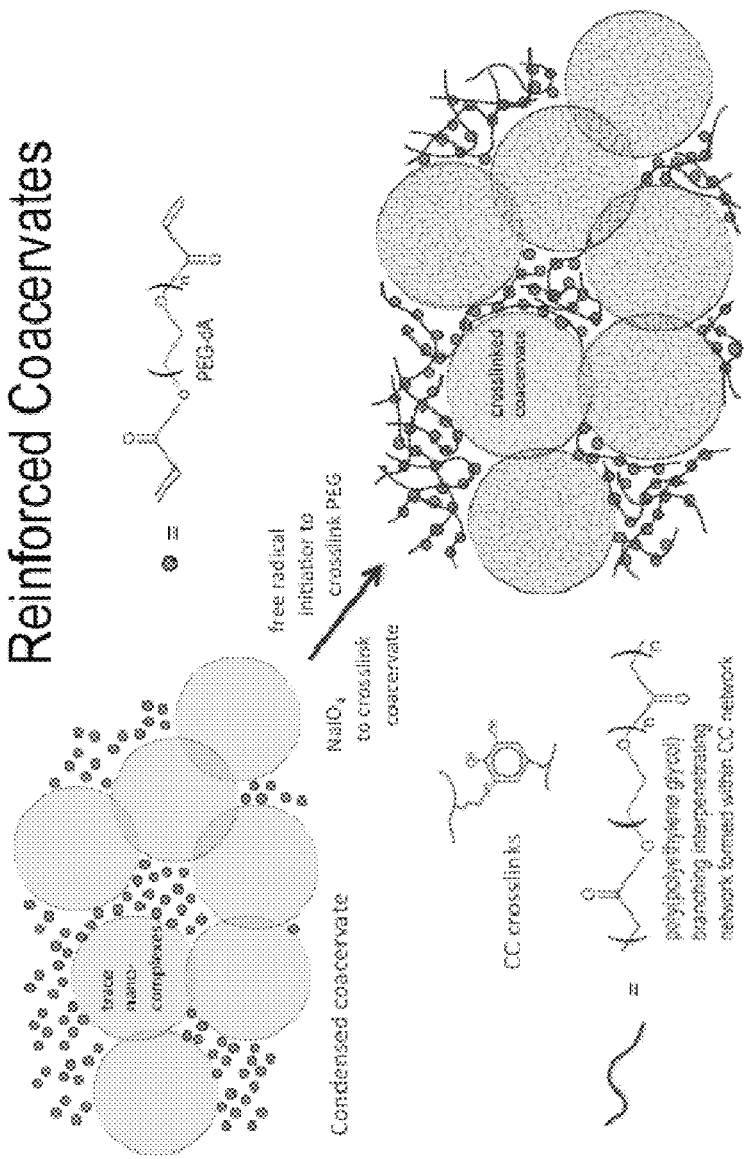
FIG. 6 shows dual crosslinking of an adhesive complex coacervate containing water-soluble polyethylene glycol polymerizable monomer. The monomer is crosslinked by free radical polymerization to form a polymer network within the complex coacervate structure. In this example, the polyanion and polycation in the complex coacervate phase are oxidatively crosslinked through ortho-dihydroxyphenyl sidechains on the polyphosphate and propyl amine sidechains on the polyamine by addition of sodium periodate.

As discussed above, the polycation and/or polyanion can be covalently attached to the interpenetrating network. For example, the polycation and polyanion can include olefinic groups capable of polymerizing with the polymerizable monomer to form a covalent bond with the interpenetrating network (FIG. 6). In other aspects, the polycation and polyanion comprises nucleophilic groups (e.g., thiols or amines) capable of reacting with groups on the interpenetrating network (e.g., olefinic groups).

In other aspects, when the reinforcing component is a filler, the filler can be functionalized such that it can form covalent or non-covalent bonds with the polycation, polyanion, and/or interpenetrating network. For example, if the filler is functionalized with olefinic groups such as acrylate groups, it can polymerize with the polymerizable monomer such that the filler is covalently bonded to the resulting interpenetrating network. Alternatively, the filler can be modified with nucleophilic groups capable of reacting with electrophilic groups on the polycation, polyanion, and/or interpenetrating network. In other aspects, the filler can possess groups that permit electrostatic interactions between the polycation, polyanion, interpenetrating network, or any combination thereof.

In general, the interpenetrating polymer network should be biodegradable and biocompatible for medical applications. Thus, the polymerizable monomer is selected such that a biodegradable and biocompatible interpenetrating polymer network is produced upon polymerization. For example, the polymerizable monomer can possess cleavable ester linkages. In one aspect, the polymerizable monomer is hydroxypropyl methacrylate (HPMA), which will produce a biocompatible interpenetrating network. In other aspects, biodegradable crosslinkers can be used to polymerize biocompatible water soluble monomers such as, for example, alkyl methacrylamides. The crosslinker could be enzymatically degradable, like a peptide, or chemically degradable by having an ester or disulfide linkage.

Figure 7:
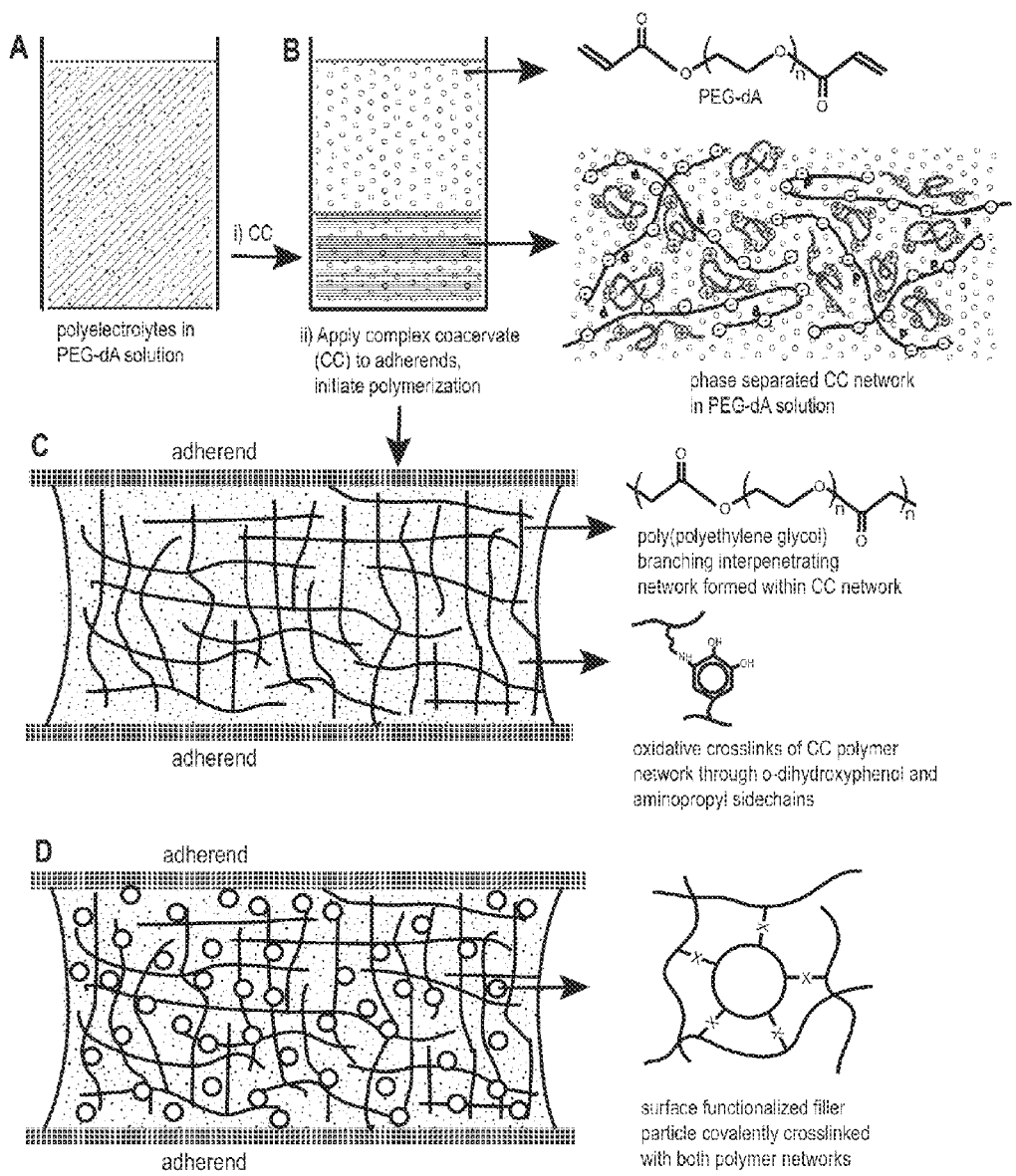
FIG. 7 shows an exemplary procedure for making the adhesive complex coacervates and adhesives described herein.

FIG. 7 provides an exemplary reaction scheme for making the coacervates and adhesives described herein. Referring to FIG. 7, a solution of polycation and polyanion (i.e., polyelectrolytes) with PEG-dA (polymerizable monomer) (step A). A coacervate is produced from this solution (step B), where the complex coacervate with PEG-dA entrapped within is a fluid at the bottom of the vial. The coacervate is applied to an adherend (i.e., substrate), and the coacervate is cured to produce the interpenetrating network (step c). FIG. 7 also depicts oxidative crosslinking of the polyelectrolytes via the oxidation of o-dihydroxyphenol and amino groups present on the polyelectrolytes. FIG. 7D also depicts surface functionalized filler particles covalently crosslinked with the interpenetrating network and polyelectrolyte network.

In other aspects, when the reinforcing component does not possess groups capable of forming a covalent bond with the coacervate, the reinforcing component can enhance the mechanical properties of the coacervate by occupying or filling gaps in the coacervate. In this aspect, the reinforcing component is physically entrapped within the coacervate. Upon removal of solvent such as, for example, water, the reinforcing component forms a rigid internal skeleton, which enhances the mechanical properties of the coacervate, The reinforced adhesive complex coacervates described herein have several desirable features when compared to conventional adhesives, which are effective in wet or underwater applications. The adhesive complex coacervates described herein can be delivered underwater without dispersing into the water because they are phase separated from water although being water-borne, they have low interfacial tension with water and wettable substrates; when applied to a wet substrate they spread over the interface rather than beading up. The adhesive complex coacervates are effective in bonding two adherends together, particularly when the adherends are wet or will be exposed to an aqueous environment. The formation of the interpenetrating network increases enhances the mechanical properties of the coacervate including, but not limited to, cohesion (i.e., internal strength), fracture toughness, extensibility, fatigue resistance, elastic modulus, etc. In other words, upon formation of the interpenetrating network, the strength of the bond between the two adherends formed by the coacervate is increased significantly. The degree of crosslinking that occurs during the curing step can vary depending upon the selection of starting materials.

VII. Kits

The polycations and polyanions described herein can be stored as dry powders for extended periods of time. This feature is very useful for preparing the coacervates and ultimately the adhesives when desired. Thus, described herein are kits for making the complex coacervates and adhesives described herein. In one aspect, the kit comprises (1) a dry polycation, (2) a dry polyanion, (3) a reinforcing component, and (4) an initiator and optional coinitiator. In another aspect, the kit comprises (1) a dry mixture of polycation and a polyanion, (2) a reinforcing component, and (3) an initiator and optional coinitiator. In a further aspect, the kit comprises (1) a dry polycation, (2) a dry polyanion, and (3) a reinforcing component, and wherein an initiator and optional coinitiator are covalently attached to the polycation and/or polyanion.

The kits can include additional components as needed such as, for example, an oxidant as described herein. When stored as dried powders, water with or without reinforcing component can be added to the polycation and/or polyanion to produce the coacervate. In one aspect, prior to lyophilizing the polycation and polyanion in order to produce a dry powder, the pH of the polycation and polyanion can be adjusted such that when they are admixed in water the desired pH is produced without the addition of acid or base. For example, excess base can be present in the polycation powder which upon addition of water adjusts the pH accordingly.

VIII. Application of the Reinforced Adhesive Complex Coacervates

Figure 9:
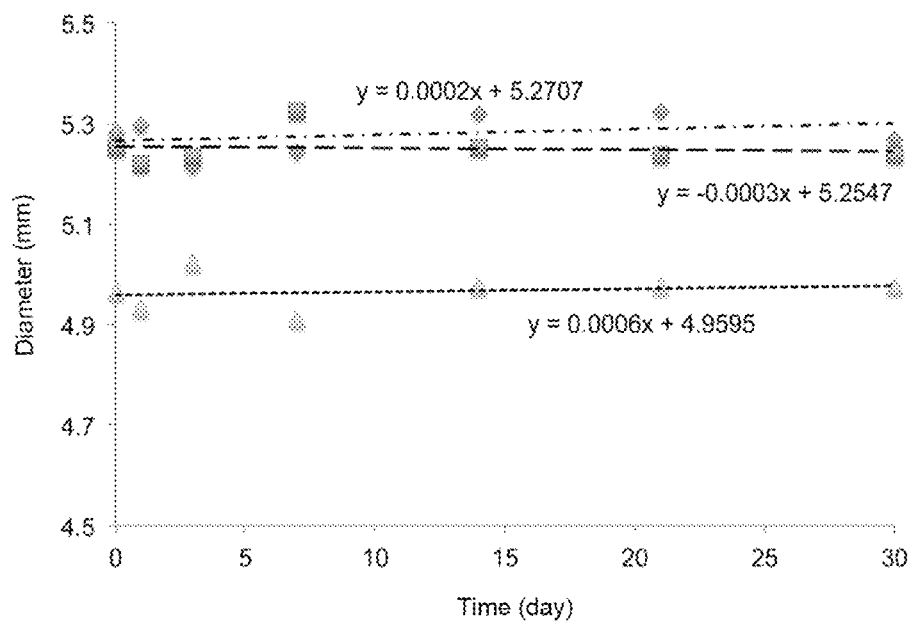
FIG. 9 shows the dimensional stability of cured adhesive complex coacervate. The coacervate was cured in an approximately 5 mm circular mold. After curing by oxidative crosslinking between the polyphosphate with pendant o-dihydroxphenyl groups and the polyamine, the circular adhesives were placed in physiological saline and the diameter measured for up to 30 days. The change in diameter was less than 1% after 30 days. The symbols represent measurements on three independently prepared samples.

The adhesive complex coacervates and adhesives described herein have numerous benefits with respect to their use as biological glues and delivery devices. For example, the coacervates have low initial viscosity, specific gravity greater than one, and containing a significant fraction of water by weight, low interfacial tension in an aqueous environment, all of which contribute to their ability to adhere to a wet surface. They are water-borne eliminating the need for potentially toxic solvents. Despite being water-borne they are phase separated from water. This allows the adhesives complex coacervate to be delivered underwater without dispersing. The adhesive complex coacervates are dimensional stable after crosslinking so that when applied in a wet physiological environment they do not swell. The lack of swelling, i.e., absorption of water, is due to the phase-separated nature of the copolymer network. FIG. 9 shows the dimensional stability of a cured adhesive complex coacervate. This is of critical importance for medical adhesives; swelling after application can cause damage to surrounding tissues and pain. Dimensional stability is a major advantage over tissue adhesives/sealants based on cross-linked PEG hydrogels. An additional advantage with respect to the bonding mechanism (i.e., crosslinking) of the adhesive complex coacervates includes low heat production during setting, which prevents damage to living tissue.

The adhesive complex coacervates described herein can be applied to a number of different biological substrates. The substrate can be contacted in vitro or in vivo. The rate of curing can be modified accordingly based upon the selection and amount of initiator used. In the case when the polyanion and polycation are capable of crosslinking with one another, the rate of crosslinking can be controlled by for example pH and the presence of an oxidant or other agents that facilitate crosslinking.

One approach for applying the adhesive complex coacervate to the substrate involves the use of a multi-compartment syringe. In one aspect, a double-compartment or -barrel syringe can be used. For example, one component can hold a mixture of the polycation and polyanion as a dry powder and the second compartment hold a solution of the polymerizable monomer. Either or both compartments can hold additional components such as the polymerization initiator, fillers, and the like. Upon mixing of the dry polycation and polyanion with the solution of polymerizable monomer, the adhesive complex coacervate is produced on site. Thus, in this aspect, the adhesive complex coacervate can be applied at distinct and specific regions of the substrate.

The properties of the adhesive complex coacervates described herein make them ideal for underwater applications such as the administration to a subject. For example, the adhesive complex coacervates and adhesives produced therefrom can be used to repair a number of different bone fractures and breaks. The coacervates adhere to bone (and other minerals) through several mechanisms. The surface of the bone's hydroxyapatite mineral phase ($Ca_5(PO_4)_3(OH)$) is an array of both positive and negative charges. The negative groups present on the polyanion (e.g., phosphate groups) can interact directly with the positive surface charges or it can be bridged to the negative surface charges through the cationic groups on the polycation and/or multivalent cations. Likewise, direct interaction of the polycation with the negative surface charges would contribute to adhesion. Additionally, when the polycation and/or polyanion contain catechol moieties, they can facilitate the adhesion of the coacervate to readily wet hydroxyapatite. Other adhesion mechanisms include direct bonding of unoxidized crosslinker (e.g., ortho-dihydroxyphenyl compounds or other catechols) to hydroxyapatite. Alternatively, oxidized crosslinkers can couple to nucleophilic sidechains of bone matrix proteins.

Examples of such breaks include a complete fracture, an incomplete fracture, a linear fracture, a transverse fracture, an oblique fracture, a compression fracture, a spiral fracture, a comminuted fracture, a compacted fracture, or an open fracture. In one aspect, the fracture is an intra-articular fracture or a craniofacial bone fracture. Fractures such as intra-articular fractures are bony injuries that extend into and fragment the cartilage surface. The adhesive complex coacervates and adhesives may aid in the maintenance of the reduction of such fractures, allow less invasive surgery, reduce operating room time, reduce costs, and provide a better outcome by reducing the risk of post-traumatic arthritis.

In other aspects, the adhesive complex coacervates and adhesives produced therefrom can be used to join small fragments of highly comminuted fractures. In this aspect, small pieces of fractured bone can be adhered to an existing bone. It is especially challenging to maintain reduction of the small fragments by drilling them with mechanical fixators. The smaller and greater number of fragments the greater the problem. In one aspect, the adhesive complex coacervate may be injected in small volumes to create spot welds as described above in order to fix the fracture rather than filling the entire crack followed by curing the adhesive complex coacervate. The small biocompatible spot welds would minimize interference with healing of the surrounding tissue and would not necessarily have to be biodegradable. In this respect it would be similar to permanently implanted hardware.

In other aspects, the adhesive complex coacervates and adhesives produced therefrom can be used to secure a patch to bone and other tissues such as, for example, cartilage, ligaments, tendons, soft tissues, organs, and synthetic derivatives of these materials. In one aspect, the patch can be a tissue scaffold or other synthetic materials or substrates typically used in wound healing applications. Using the complexes and spot welding techniques described herein, the adhesive complex coacervates and adhesives produced therefrom can be used to position biological scaffolds in a subject. Small adhesive tacks composed of the adhesive complex coacervates described herein would not interfere with migration of cells or transport of small molecules into or out of the scaffold. In certain aspects, the scaffold can contain one or more drugs that facilitate growth or repair of the bone and tissue. In other aspects, the scaffold can include drugs that prevent infection such as, for example, antibiotics. For example, the scaffold can be coated with the drug or, in the alternative, the drug can be incorporated within the scaffold so that the drug elutes from the scaffold over time.

The adhesive complex coacervates and adhesives produced therefrom have numerous dental applications. For example, the adhesive complex coacervates can be used to seal breaks or cracks in teeth, for securing crowns, or allografts, or seating implants and dentures. The adhesive complex coacervate can be applied to a specific points in the mouth (e.g., jaw, sections of a tooth) followed by attaching the implant to the substrate and subsequent curing.

In other aspects, the adhesive complex coacervates and adhesives produced therefrom can adhere a substrate to bone. For example, implants made from titanium oxide, stainless steel, or other metals are commonly used to repair fractured bones. The adhesive complex coacervate can be applied to the metal substrate, the bone, or both prior to adhering the substrate to the bone. In certain aspects, the crosslinking group present on the polycation or polyanion can form a strong bond with titanium oxide. For example, it has been shown that DOPA can strongly bind to wet titanium oxide surfaces (Lee et al., PNAS 103:12999 (2006)). In other aspects, the substrate can be a fabric (e.g., an internal bandage), a tissue graft, or a wound healing material. Thus, in addition to bonding bone fragments, the adhesive complex coacervates described herein can facilitate the bonding of substrates to bone, which can facilitate bone repair and recovery.

It is also contemplated that the adhesive complex coacervates and adhesives produced therefrom can encapsulate one or more bioactive agents. The bioactive agents can be any drug including, but not limited to, antibiotics, pain relievers, immune modulators, growth factors, enzyme inhibitors, hormones, mediators, messenger molecules, cell signaling molecules, receptor agonists, or receptor antagonists.

In another aspect, the bioactive agent can be a nucleic acid. The nucleic acid can be an oligonucleotide, deoxyribonucleic acid (DNA), ribonucleic acid (RNA), or peptide nucleic acid (PNA). The nucleic acid of interest can be nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature.

In other aspects, the bioactive agent is used in bone treatment applications. For example, the bioactive agent can be bone morphogenetic proteins (BMPs) and prostaglandins. When the bioactive agent is used to treat osteoporosis, bioactive agents known in the art such as, for example, bisphonates, can be delivered locally to the subject by the adhesive complex coacervates and adhesives described herein.

In certain aspects, the filler used to produce the coacervate can also possess bioactive properties. For example, when the filler is a silver particle, the particle can also behave as an anti-bacterial agent. The rate of release can be controlled by the selection of the materials used to prepare the complex as well as the charge of the bioactive agent if the agent is a salt. Thus, in this aspect, the insoluble solid can perform as a localized controlled drug release depot. It may be possible to simultaneously fix tissue and bones as well as deliver bioactive agents to provide greater patient comfort, accelerate bone healing, and/or prevent infections.

The adhesive complex coacervates and adhesives produced there from can be used in a variety of other surgical procedures. For example, adhesive complex coacervates and adhesives produced therefrom can be used to treat ocular wounds caused by trauma or by the surgical procedures. In one aspect, the adhesive complex coacervates and adhesives produced therefrom can be used to repair a corneal or schleral laceration in a subject. In other aspects, adhesive complex coacervates can be used to facilitate healing of ocular tissue damaged from a surgical procedure (e.g., glaucoma surgery or a corneal transplant). The methods disclosed in U.S. Published Application No. 2007/0196454, which are incorporated by reference, can be used to apply the coacervates described herein to different regions of the eye.

In other aspects, the adhesive complex coacervates and adhesives produced therefrom can be used to inhibit blood flow in a blood vessel of a subject. In general, the adhesive complex coacervate is injected into the vessel followed by polymerizing the polymerizable monomer as described above to partially or completely block the vessel. This method has numerous applications including hemostasis or the creation of an artificial embolism to inhibit blood flow to a tumor or aneurysm or other vascular defect.

The adhesive complex coacervates described herein to seal the junction between skin and an inserted medical device such as catheters, electrode leads, needles, cannulae, osseo-integrated prosthetics, and the like. In this aspect, the coacervates prevent infection at the entry site when the device is inserted in the subject. In other aspects, the coacervates can be applied to the entry site of the skin after the device has been removed in order to expedite wound healing and prevent further infection.

In another aspect, the adhesive complex coacervates described herein can be used to close or seal a puncture in an internal tissue or membrane. In certain medical applications, internal tissues or membranes are punctured, which subsequently have to be sealed in order to avoid additional complications. Alternatively, the adhesive complex coacervates described herein can be used to adhere a scaffold or patch to the tissue or membrane in order to prevent further damage and facilitate wound healing.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Methods

Coacervate Formation

The adhesive coacervate was formed with two crosslinking polymer systems. First, a positively charged polyamine and negatively charged polyphosphate containing 20 mol % dopamide sidechains (polyphosphodopa) that associate into a complex coacervate. Second, a monomer that when polymerized forms a polymer network within the coacervate matrix. Polyethylene glycol (PEG) diacrylate was used as the polymerizable monomer. Aqueous PEG diacrylate solutions were prepared by dissolving various amounts of PEG diacrylate (0, 5, 10, 15, 20, or 25 wt %) in degassed deionized water. A 50 mg/ml aqueous polyamine solution was prepared by dissolving the polyamine in a PEG diacrylate solution of a given wt %. A 50 mg/ml aqueous polyphosphodopa solution was prepared by dissolving the polymer in a given wt % of PEG diacrylate. Calcium chloride stock solution was added to a $Ca^{2+}$ to phosphate molar ratio of 0.2. The pH of the polyamine and polyphosphate solutions was adjusted to 7.4±0.2 with NaOH. While stirring, the polyamine solution was added dropwise into the polyphosphate solution with a fixed amine to phosphate ratio of 0.6. The solution appeared cloudy at first. Within a few minutes the coacervate phase settled to the bottom with a clear supernatant at the top. The supernatant was then removed from the top.

Mechanical Bond Testing

Figure 8:
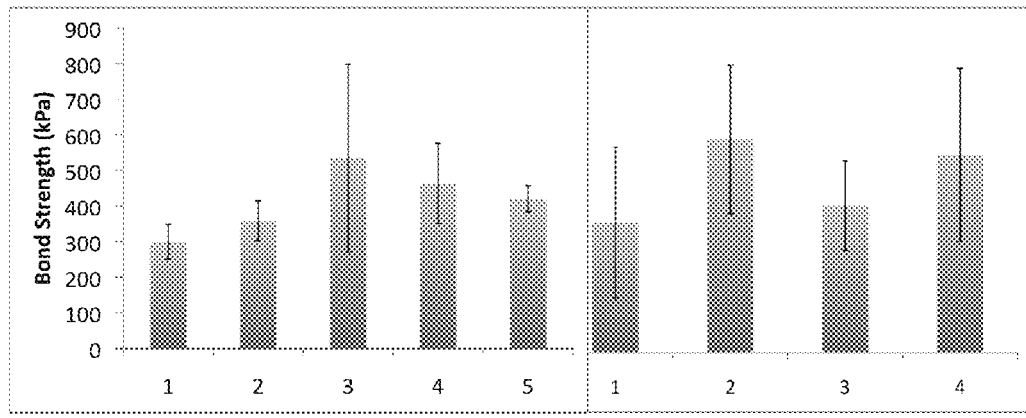
FIG. 8 shows bond strengths of multi-phase adhesives. Left panel: column 1-5, complex coacervates were formed in 5, 10, 15, 20 25 wt % PEG-diacrylate, respectively. Right panel: 10 wt % PEG-diacrylate gels with various filler particles. Column 1, silica microparticles; column 2, methacrylate modified silica microparticles; column 3, barium sulfate microparticles; column 4, methacrylate modified barium sulfate microparticles. Bond strengths are highest with surface modified fillers (columns 2 and 4).

To test the bond strength of the glue, 5052 aluminum substrates of dimensions 0.5×5 cm were used. The substrates were polished with 600 grit sand paper followed by cleaning in methanol under sonication for 10 minutes twice, air-dried, dipped into sulfuric acid for 15 minutes, rinsed with deionized water, and stored in deionized water until bonding. Curing agents were added to the adhesive coacervate before application onto the aluminum substrates. The dopamide (DOPA) sidechains in the polyphosphate were oxidatively crosslinked with sodium periodate ($NaIO_4$). To slow down the oxidation reaction the $NaIO_4$ was complexed with the sugar 1,2-O-IsoProPylidene-D-glucofuranose. An aqueous solution of $NaIO_4$/sugar complex solution (100 mg/ml) with a $NaIO_4$:sugar of 1:1.2 was prepared in DI water. APS (Ammonium persulfate) and TEMED (N, N, N', N'-Tetramethylethylenediamine) were used to initiate polymerization of the PEG diacrylate monomer within the coacervate. An aqueous 10 mg/ml APS stock solution was prepared. A TEMED stock solution was made by dissolving 10 µl of TEMED in 990 µl of DI water. Each 100 µl of coacervate was cured by adding 10 µl APS stock solution, 10 µl of TEMED stock solution, and the $NaIO_4$/sugar complex at a molar ratio of $NaIO_4$:DOPA of 1:1. For each type of coacervate the bond strength of 5 samples were measured. In each sample 20 µl of oxidized coacervate is applied to wet substrate using a pipette, which is then overlapped with another substrate varying from 14-20 mm, clamped, and immediately submerged in water. The bonded specimens submerged in water are than cured for 20 hours at 37° C. An Instron 3342 materials testing system with a 100 N load cell was used to test the shear strengths of the samples. The samples while tested were submerged in a temperature controlled water bath. After failing, the area of the applied glue is measured to obtain the bond strength (kPa) of the coacervate (FIG. 8A). The highest bond strength was observed at 15 wt % PEG-diacrylate.

In another experiment, filler particles were added to the polyelectrolyte solution before coacervate phase separation composed of 10 wt % PEG-diacrylate. Bond strengths are shown in FIG. 8B. In general, the bond strengths of the coacervates increased with the filler compared to the same coacervate that did not contain filler. The highest bond strength was observed when the filler was methacrylate modified silica, which crosslinked with the PEG interpenetrating network.

Second Procedure for Preparing Adhesives

Labels of Pre-Weighed Component Tubes

| Label | Material |
|---|---|
| −4 | Polyphosphate powder |
| +4 | Polyamine powder |
| M | Monomer Solution |
| A | APS |
| T | TEMED |
| N | $NaIO_4$ |
| S1 | Sugar[a] (Sugar:$NaIO_4$ 1:1) |
| S2 | Sugar[a] (Sugar:$NaIO_4$ 1.1:1) |
| S3 | Sugar[a] (Sugar:$NaIO_4$ 1.2:1) |

[a]Sugar is 1,2-O-IsoProPylidene-D-glucofuranose.

Preparing the Adhesive Coacervate

1. The polymers have been pre-weighed in individual eppendorf tubes to produce 200 µl of coacervate. Dissolve the pre-weighed polyphosphate (tube labeled −4) in 500 µl 20% monomer solution (M).
2. Dissolve the pre-weighed polyamine (+4) in 500 µl of DI water.
3. Slowly add the polyamine solution (+4) into the polyphosphate solution (−4) drop-wise while vortexing. The solution will immediately turn cloudy.
4. The fluid coacervate phase will settle to the bottom of the tube within a few minutes. The top phase will be almost clear. There should be ~200 µl of coacervate and 800 µl of the upper clear phase (pH~7.4). Remove the top layer with a pipette.
5. Using a 100 µl positive displacement pipette transfer 100-200 µl of coacervate into a 1000 µl tip that has a plastic plug in the bottom opening.

Preparing Curing Solutions

6. Prepare ammonium persulfate (APS) stock solution (10 mg/ml) by adding 100 µl of DI water per mg of pre-weighed APS (tubes labeled A). The APS weight in mg is written on the side of the tubes. (e.g., add 243 µl DI water to 2.43 mg).
7. Prepare a TEMED (T) stock solution by adding 10 ml of TEMED (bottle labeled T) to 990 µl of DI water and mixing.
8. Prepare a sodium periodate/sugar complex (NS) stock solution.**

**Three different sugar amounts were prepared to control the rate of the curing reaction. The higher the ratio (number on the tube) the slower the cure rate.

a. Add 200 µl of DI water to pre-weighed sugar (tubes labeled S1, S2, or S3).
   b. Mix sugar solution into the pre-weighed sodium periodate (tube labeled N).
9. Prepare a periodate/sugar complex and TEMED (NST) stock solution by mixing 20 µl of T stock solution with 22 µl of NS stock solution.

Applying the Adhesive Coacervate

10. Into each 100 µl of coacervate within the plugged tip add:
    a. 10 µl of stock solution A and mix.
    b. 21 µl stock solution NTS and mix quickly and thoroughly.
    c. Place "nicked" plunger into pipette tip. While holding pipette tip pointing up remove the plastic plug from the end.
    d. Apply the glue within a couple minutes. The adhesive turns reddish brown as it cures. The color change can be used to judge when to apply the adhesive (no color=too early, dark brown=too late).

The polymer tubes wrapped in parafilm were prepared under sterile conditions for use in toxicity tests. Steps 1-10 should be done with sterile tips, solutions, etc.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for inhibiting blood flow in a blood vessel of a subject comprising introducing as associative liquid adhesive complex coacervate into the vessel, wherein the complex coacervate comprises (a) at least one polycation, (b) at least one polyanion, and (c) a reinforcing component.

2. The method of claim 1, wherein the polycation comprises a polyamino compound.

3. The method of claim 1, wherein the polycation comprises a polysaccharide, a natural protein, a recombinant protein, or a synthetic polyamine.

4. The method of claim 1, wherein the polycation comprises an alkylamino group, a heteroaryl group, a guanidinyl group, or an aromatic group substituted with one or more amino groups.

5. The method of claim 1, wherein the polycation comprises a natural protein.

6. The method of claim 5, wherein the natural protein comprises one or more guanidinyl groups.

7. The method of claim 1, wherein the polycation comprises a polymer comprising at least one fragment comprising the formula I

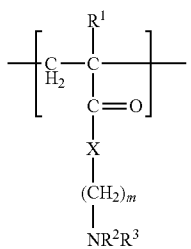

wherein $R^1$, $R^2$, and $R^3$ are, independently, hydrogen or an alkyl group, X is oxygen or $NR^5$, where $R^5$ is hydrogen or an alkyl group, and m is from 1 to 10, or the pharmaceutically-acceptable salt thereof.

8. The method of claim 7, wherein $R^1$, $R^2$, and $R^3$ are methyl, X is O, and m is 3.

9. The method of claim 1, wherein the polyanion comprises two or more sulfate, sulfonate, carboxylate, borate, boronate, phosphonate, or phosphate groups.

10. The method of claim 1, wherein the polyanion comprises a polyphosphate.

11. The method of claim 10, wherein the polyphosphate comprises a natural polymer or a synthetic polymer.

12. The method of claim 10, wherein the polyphosphate comprises a polyacrylate comprising one or more pendant phosphate groups.

13. The method of claim 1, wherein the polyanion comprises a polymer comprising at least one fragment comprising the formula X

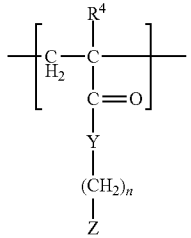

wherein $R^4$ is hydrogen or an alkyl group;
n is from 1 to 10;

Y is oxygen, sulfur, or $NR^{30}$, wherein $R^{30}$ is hydrogen, an alkyl group, or an aryl group;
Z is an anionic group or a group that can be converted to an anionic group,
or the pharmaceutically-acceptable salt thereof.

14. The method of claim 13, wherein Z is sulfate, sulfonate, carboxylate, borate, boronate, a substituted or unsubstituted phosphate, or a phosphonate.

15. The method of claim 1, wherein the polyanion comprises a polymer comprising at least one fragment comprising the formula II

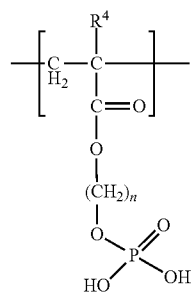

wherein $R^4$ is hydrogen or an alkyl group, and n is from 1 to 10, or the pharmaceutically-acceptable salt thereof.

16. The method of claim 15, wherein $R^4$ is methyl and n is 2.

17. The method of claim 1, wherein the reinforcing component comprises a particle, wherein the particle comprises a metal oxide, a ceramic particle, a silica particle, or a water insoluble inorganic salt.

18. The method of claim 1, wherein the reinforcing component comprises a fiber.

19. The method of claim 1, wherein the reinforcing component comprises a metal oxide particle.

20. The method of claim 1, wherein the reinforcing component comprises a metal particle.

21. The method of claim 20, wherein the metal particle is platinum, gold, or tantalum.

22. The method of claim 1, wherein the polycation comprises a natural protein comprising one or more guanidinyl groups, the polyanion comprises a polyphosphate, and the reinforcing component comprises a metal particle.

23. The method of claim 1, wherein the associative liquid adhesive complex coacervate further comprises a bioactive agent selected from the group consisting of a nucleic acid, an antibiotic, a pain reliever, an immune modulator, a growth factor, an enzyme inhibitor, a hormone, a mediator, a messenger molecule, a cell signaling molecule, a receptor agonist, and a receptor antagonist, wherein the bioactive agent is encapsulated in the associative liquid adhesive complex coacervate.

* * * * *